US009176380B2

(12) United States Patent
Bowman et al.

(10) Patent No.: US 9,176,380 B2
(45) Date of Patent: Nov. 3, 2015

(54) PHOTOINDUCED ALKYNE-AZIDE CLICK REACTIONS

(75) Inventors: Christopher Bowman, Boulder, CO (US); Brian A. Adzima, Boulder, CO (US); Christopher J. Kloxin, Boulder, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 71 days.

(21) Appl. No.: 13/990,218

(22) PCT Filed: Nov. 28, 2011

(86) PCT No.: PCT/US2011/062248
§ 371 (c)(1),
(2), (4) Date: Aug. 19, 2013

(87) PCT Pub. No.: WO2012/074931
PCT Pub. Date: Jun. 7, 2012

(65) Prior Publication Data
US 2013/0323642 A1    Dec. 5, 2013

Related U.S. Application Data

(60) Provisional application No. 61/417,785, filed on Nov. 29, 2010.

(51) Int. Cl.
*C07D 249/04*    (2006.01)
*G03F 7/20*      (2006.01)
*G03F 7/008*     (2006.01)

(52) U.S. Cl.
CPC ............ *G03F 7/0085* (2013.01); *C07D 249/04* (2013.01); *G03F 7/20* (2013.01)

(58) Field of Classification Search
CPC ........ C07D 249/04; G03F 7/20; G03F 7/0085
USPC ................................................ 430/270.1, 325
See application file for complete search history.

(56) References Cited

U.S. PATENT DOCUMENTS 6,727,034 B1 *    4/2004    Ogiso et al. .................... 430/176
2008/0045686 A1 *    2/2008    Meagher et al. ........... 526/329.7

OTHER PUBLICATIONS

Himo et al., Copper(I)-Catalyzed Synthesis of Azoles. DFT Study Predicts Unprecedented Reactivity and Intermediates, Contribution from the Department of Molecular Biology, and Department of Chemistry and The Skaggs Institute for Chemical Biology, The Scripps Research Institute, Published on Web Dec. 8, 2004.*
International Search Report dated Apr. 5, 2012, for PCT International Application No. PCT/US11/62248, filed Nov. 28, 2011.
(Continued)

*Primary Examiner* — Brittany Raymond
(74) *Attorney, Agent, or Firm* — Saul Ewing LLP; Kathryn Doyle; Domingos J. Silva

(57) ABSTRACT

The present invention includes a composition comprising an alkyne-based substrate, an azide-based substrate, a Cu(II) salt and a photoinducible reducing agent. The present invention further includes a method of immobilizing a chemical structure in a given pattern onto a section of the surface of a solid substrate, using the photoinducible Cu(I)-catalyzed azide-alkyne cycloaddition Click reaction.

11 Claims, 15 Drawing Sheets

(56) References Cited

OTHER PUBLICATIONS

Kunkely, H. et al., "Photoredox Reactivity of Copper(II)-3,5-Diisopropylsalicylate Induced by Ligand-to-Metal Charge Transfer Excitation of the Copper-Phenolate Chromophore," Inorganica Chimica Acta, vol. 357, pp. 888-890, 2004.

Perera, M.D.A., "Development of Clickable Approaches to Build Functional Polymeric Nanoparticles," Thesis submitted to the University of Nottingham, The University of Nottingham School of Pharmacy, Nottingham, UK, 2009.

Ritter, S.C., "Cu(I)-Catalyzed 'Click Chemistry' Design of a Chemical Photomultiplier Target-Guided Synthesis of Bidentate Metal-Complex Receptors," Thesis submitted to the University of Regensburg, Universität Regensburg, Germany, 2007.

Tasdelen, M.A. et al., "Light-Induced Copper(I)-Catalyzed Click Chemistry," Tetrahedron Letters, 2010.

* cited by examiner (C)

(D)

PHOTOINDUCED ALKYNE-AZIDE CLICK REACTIONS

CROSS-REFERENCE TO RELATED APPLICATION

The present application is a 35 U.S.C. §371 national phase application of, and claims priority to, International Application No. PCT/US2011/62248, filed Nov. 28, 2011, and published under PCT Article 21(2) in English, which claims priority under 35 U.S.C. §119(e) to U.S. Provisional Application No. 61/417,785, filed Nov. 29, 2010, all of which applications are hereby incorporated by reference in their entireties herein.

STATEMENT REGARDING FEDERALLY SPONSORED RESEARCH OR DEVELOPMENT

The invention was made with government support under grant number CBET0933828 awarded by the National Science Foundation. The government has certain rights in the invention.

BACKGROUND OF THE INVENTION

Click chemistry is a chemical philosophy proposed in 2001 (Kolb et al., 2001, Angew. Chem.-Int, Edit. 40(11):2004-24 whereby the chemistry is tailored to generate molecules quickly and reliably by joining smaller units together. The Click reaction paradigm is centered on the development and implementation of robust reactions that proceed with reliable control over the products formed.

The Click chemistry paradigm requires the following characteristics in the reactions under consideration: the reaction involves minimal set-up effort and the starting materials are readily available; the reaction is high yielding, proceeding with high stereospecificity and high atom economy; the reaction is run solvent-free or in a benign solvent (preferably water); the product can be easily isolated by crystallization or distillation, preparative chromatography not being required; the by-products are easily removed and non-toxic; the reaction is physiologically compatible; and there is a large thermodynamic driving force (>84 kJ/mol) to favor the formation of a single reaction product. It is unlikely that any reaction will meet all these criteria for every situation. However, several reactions have been identified as generally meeting all these criteria.

One such reaction is the azide-alkyne Huisgen cycloaddition, which is a 1,3-dipolar cycloaddition between an azide and a terminal or internal alkyne to give a 1,2,3-triazole (Huisgen, 1961, Proc. Chem. Soc. London:357), Once described as "the cream of the crop" of Click chemistry, this reaction is arguably the most prolific and powerful of them (Kolb et al., 2001, Angew, Chem.-Int. Edit. 40(11):2004-24

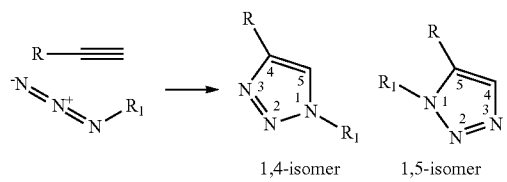

1,4-isomer    1,5-isomer

A notable variant of the Huisgen 1,3-dipolar cycloaddition is the copper(I) catalyzed (or Cu(I)-catalyzed) variant, in which organic azides and terminal alkynes are united to afford 1,4-regioisomers of 1,2,3-triazoles as sole products. The Cu(I)-catalyzed variant was first reported for solid phase synthesis of peptidotriazoles (Tornøe et al., 2002, J. Org. Chem. 67:3057-64). While the Cu(I)-catalyzed variant gives rise to a triazole from a terminal alkyne and an azide, formally it is not a 1,3-dipolar cycloaddition and thus should not be termed a Huisgen cycloaddition. This reaction is better termed the Cu(I)-catalyzed Azide-Alkyne Cycloaddition (CuAAC).

CuAAC is ubiquitous and highly efficient in an ever increasing number of synthetic methodologies and applications, including bioconjugation (Wang et al., 2003, J. Am. Chem., Soc. 125(11)3192; El-Sagheer & Brown, 2010, Chem. Soc. Rev. 39(4):1388), labeling (Macpherson et al., 2007, Nature 445(7127):541; Cohen et al., 2007, Nat. Chem. Biol. 3(3):156), surface functionalization (Spruell et al., 2008, Angew. Chem.-Int. Edit, 47(51):9927), dendrimer synthesis (Peng et al., 2004, Angew. Chem.-Int. Edit. 43(30):3928), polymer synthesis (DeForest et al., 2009, Nat. Mat. 8(8):659), and polymer modification (Matyjaszewski & Tsarevsky, 2009, Nat. Chem. 1(4):276). The diverse implementation of the CuAAC reaction is due to its simplicity, capability of high yield, fast reaction kinetics, orthogonal reactivity, and tolerance to a wide variety of solvent conditions.

The CuAAC reaction may be run in a variety of solvents, such as aqueous solvents and (partially or fully) miscible organic solvents. The starting reagents need not be completely soluble for the reaction to be successful, and in many cases the product may be simply filtered from the solution as the only purification step required.

The CuAAC reaction may be performed using commercial sources of Cu(I) such as cuprous bromide or iodide, or in situ sources of Cu(I), such as a mixture of Cu(II) (e.g. copper(II) sulfate) and a reducing agent (e.g. sodium ascorbate). Since the Cu(I) catalyst is either directly added to the reaction bulk or generated by chemical reduction of Cu(II), temporal and/or spatial control of the CuAAC reaction is extremely limited at this point. While this deficit may seem trivial from a purely synthetic point of view, such control is necessitated in the creation of numerous functional materials (Bowman & Kloxin, 2008, AICHE J. 54(11):2775; Hoyle & Bowman, 2010, Angew. Chem.-Int. Edit. 49(9):1540) such as inks, coatings, adhesives, metamaterials, contact lenses, dental materials, and photoresists, and is employed in techniques such as parallel protein synthesis (Fodor et al., 1991, Science 251(4995):767), cell encapsulation (Koh et al., 2002, Langmuir 18(7):2459), tissue engineering (Martens et al., 2003, Biomacromol. 4(2):283), and 3D prototyping (Neckers, 1992, Polym. Eng. Sci. 32(20):1481; Young et al., 1999, J. Mina Sci. Eng.-Trans. ASME 121(3):474).

The CuAAC reaction mechanism is understood as involving three general steps: (I) the Cu(I)-acetylide formation, (II) the formal cycloaddition, and (III) catalyst regeneration (FIG. 1A) (Rodionov et al., 2007, JACS 129:12705-12712; Rostovtsev et al., 2002, Angew. Chem.-Int. Edit. 41:2596-2599; Himo et al., 2005, JACS 127:210-216). Under saturated conditions, where catalyst turnover is not required, the CuAAC reaction shows first order dependence on both azide and alkyne concentrations, consistent with an elementary bimolecular reaction (Rodionov et al., 2005, Angew. Chem.-Int. Edit, 44:2210-2215). In contrast, the kinetics are highly dependent on any ligands, buffer, salts, and substrates present when catalytic concentrations of Cu(I) are utilized (Rodionov et al., 2007, JACS 129:12705-12712). This behaviour has been interpreted as the consequence of a diverse family of copper coordination complexes that are formed in situ (Rodionov et al., 2007, JACS 129:12705-12712). In general, these copper species are highly reactive as evidenced by the consistent copper catalysis of the reaction for a large variety of terminal alkynes, but the reactivity of these species varies subtly to influence which step is rate-limiting.

Cu(I) is typically generated using sodium ascorbate as a reductant, which is used in large excess (10:1) to compensate for oxidation and disproportionation of Cu(I) (Himo et al., 2005, JACS 127:210-216; Chan et al., 2004, Org. Lett. 6:2853-2855). As such, nearly quantitative reduction of Cu(II) is assumed to occur. It is perhaps surprising, given the CuAAC reaction's susceptibility to other species, that the ascorbate anion appears to have no effect on the reaction kinetics (Rodionov et al., 2007, JACS 129:12705-12712). The radical mediated reduction of Cu(II) to copper metal has recently attracted renewed interest for both removal of hazardous wastes and generation of copper nanoparticles (Litter, 1999, Appl. Catal. B-Environ. 23:89-114; Sakamoto et al., 2008, Chem. Mater. 20:2060-2062). Due to Cu(II)/Cu(I)'s half reaction (reduction) potential of 0.16 V, a variety of organic radicals are capable of reducing it, e.g. ketyl, phosphinoyl, and semi-pinacol radicals generated by common photoinitiators such as bis(acyl)phosphines, α-hydroxyl ketones, and benzophenone. The reaction is typically described as occurring via the reduction of Cu(II) to Cu(I), followed by subsequent reduction to copper metal (reactions R1 and R2, respectively in FIG. 1A) (Kateda et al., 1968, Bull. Chem. Soc. Jpn. 41:268; Sakamoto et al., 2009, J. Photochem. Photobiol. C-Photochem. Rev. 10:33-56). Besides further reduction to copper metal, Cu(I) is both air sensitive and prone to disproportionation (reaction D in FIG. 1A) (Simmons et al., 1980, J. Chem. Soc.-Dalton Trans. 1827-1837). It would be expected that all three of these reactions could play a complicated role in the photo-mediated catalysis of the CuAAC reaction.

The critical need for complete spatial control of the CuAAC reaction is demonstrated by the extent to which researchers have gone to facilitate partial control of this reaction. Dip-pen lithography, with a Cu(I) inked tip or a copper tip (Long et al., 2007, Adv. Mater. 19(24):4471; Paxton et al., 2009, J. Am. Chem. Soc. 131(19):6692), has been used to trace a pattern on the substrate, and catalyze the CuAAC reaction between a functionalized surface, and the alternate Click reagent in the bulk. This technique has produced features as small as 50 nm, and micron scale features require one half second to complete. Similarly, microcontact printing utilizes an elastomeric stamp inked with a solution of reagent to promote spatial control (Rozkiewicz et al., 2006, Angew. Chem.-Int. Edit. 45(32):5292). The catalytic Cu(I) was either included in the solution, or generated from a copper metal layer coating the surface of the stamp. The stamp was brought into contact with a functionalized surface for minutes to an hour. Features on the order of tens of microns were fabricated using this technique. Electroclick chemistry utilizes an electric potential applied across a pair of electrodes (Devaraj et al., 2006, J. Am. Chem. Soc. 128(6):1794; Hansen et al., 2009, Adv. Mater. 21(44):4483). At the negative electrode Cu(II) was reduced to Cu(I) and the CuAAC reaction was subsequently catalyzed where features as small as 10 microns have been produced. These techniques unfortunately had drawbacks. Microcontact printing utilizes inexpensive elastomeric stamps than can rapidly reproduce images. However, the master stamps must be fabricated by another technique that is capable of directly writing the master. Electroclick chemistry shares this drawback. Dip-pen lithography is capable of directly writing high fidelity images, but is accordingly ill-suited to the reproduction of large images and features.

Alternatively, photolithography utilizes masked or focused light to irradiate a specific area, and induce chemical reactions that change the solubility of the photosensitive material. An image is then developed by immersion in a solvent. Photolithography may be directly used to both write images and reproduce images, even utilizing masks produced by inkjet printers (Qin et al., 1996, Adv. Mater. 8(11):917). Photolithography may also be used to produce three-dimensional images and reactions (Neckers, 1992, Polym. Eng. Sci. 32(20):1481; Young et al., 1999, J. Manuf. Sci. Eng.-Trans. ASME 121(3):474), to write images within a material (DeForest et al., 2009, Nat. Mat. 8(8):659) and to functionalize a material anywhere throughout the material. There have been no reports of generation of polymeric network-forming materials via CuAAC crosslinking reactions by conventional photolithographic methods.

Photochemical reactions have long attracted attention from synthetic chemists because these reactions allow the assembly of complex systems under mild conditions. Upon irradiation, photochemical reactions occur either by direct excitation of chromophoric species, as in the case of [2+2] cycloadditions, or by the generation of an active species that initiates multiple reactions, as typical of photopolymerizations. Photochemical 1,3-cycloadditions are symmetry forbidden (Padwa, 1976, Angew. Chem.-Int. Edit. Engl 15(3):123) and the photopatterning of azides and alkynes has been limited to the photochemical decarbonylation of propenones to dibenzocyclooctynes, which subsequently undergo the thermal 1,3-dipolar cycloaddition (copper-free azide-alkyne Click reaction) (Poloukhtine et al., 2009, J. Am. Chem. Soc. 13 (43):15769). Despite the success of this innovative approach for labeling cells (Poloukhtine et al., 2009, J. Am. Chem. Soc. 13 (43):15769) and functionalizing surfaces (Orski et al., 2010, J. Am. Chem. Soc. 13(32)11024), this approach is limited by the complexity and scarcity of materials possessing the requisite cyclopropenone functional group, the synthesis of which is non-trivial. Furthermore, this approach requires large irradiation doses to obtain high conversions, as each absorbed photon leads to a maximum of one bimolecular coupling event. In contrast, unprotected, reactive azides are readily synthesized from acyl halides, and typical photoinitiated polymerizations follow a chain reaction mechanism, where a single absorbed photon leads to a reaction cascade that ultimately consumes many reactant molecules per absorbed photon.

There is a need in the art to develop a novel method of catalyzing the CuAAC reaction that can be spatially and temporally controlled. This robust and controllable reaction would be a much needed addition to the repertoire of synthetic transformations available to synthetic chemists and material scientists. This reaction would find application not only in conventional small molecule synthesis but in surface modification, polymerization reactions and polymer modification reactions as well. The present invention fulfills this need.

BRIEF SUMMARY OF THE INVENTION

The invention includes a composition comprising an alkyne-based substrate, an azide-based substrate, at least one Cu(II) salt and at least one photoinducible reducing agent, wherein: the alkyne-based substrate comprises at least one reactive alkynyl group, and the azide-based substrate comprises at least one reactive azide group.

In one embodiment, the alkyne-based substrate or the azide-based substrate is attached to a hydrogel. In another embodiment, the at least one reactive alkynyl group is a terminal alkynyl group. In yet another embodiment, the molar ratio of the at least one reactive alkyne group and the at least reactive azide group in the composition ranges from about $10^{-2}$ to about $10^{+2}$. In yet another embodiment, the at least one photoinducible reducing agent is a Type (I) photoinitiator. In yet another embodiment, the at least one reducing agent is selected from the group consisting of: 1-hydroxy-cyclohexyl-phenyl-ketone; benzophenone; 2-hydroxy-2-methyl-1-phenyl-1-propanone; 2-hydroxy-1-[4-(2-hydroxyethoxy)phenyl]-2-methyl-1-propanone; methyl benzoylformate; oxy-phenyl-acetic acid 2-[2-oxo-2-phenyl-acetoxy-ethoxy]-ethyl ester; oxy-phenyl-acetic 2-[2-hydroxy-ethoxy]-ethyl ester; oxy-phenyl-acetic acid 2-[2-oxo-2-phenyl-acetoxy-ethoxy]-ethyl ester; alpha,alpha-dimethoxy-alpha-phenylacetophenone; 2-benzyl-2-(dimethylamino)-1-[4-(4-morpholinyl) phenyl]-1-butanone; 2-methyl-1-[4-(methylthio)phenyl]-2-(4-morpholinyl)-1-propanone; diphenyl(2,4,6-trimethylbenzoyl)-phosphine oxide; bis-(eta 5-2,4-cyclopentadien-1-yl)-bis-[2,6-difluoro-3-(1H-pyrrol-1-yl)-phenyl]titanium; (4-methylphenyl) [4-(2-methylpropyl) phenyl]-iodonium hexa fluorophosphate; 2-(4-methylbenzyl)-2-(dimethylamino)-1-(4-morpholinophenyl)-butan-1-one; 4-(2-hydroxyethoxy)phenyl-(2-hydroxy-2-propyl)-ketone; bis-(2,6-dimethoxybenzoyl)-2,4,4-trimethylpentyl phosphine oxide; titanium dioxide; and mixtures thereof.

The invention also includes a method of preparing a compound of formula (I):

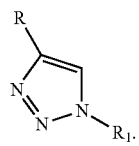

(I)

The method comprises the step of mixing a compound of formula (II):

R—C≡C—H (II), a compound of formula (III):

 (III), at least one Cu(II) salt and at least one photoinducible reducing agent, to generate a first composition, wherein R and $R_1$ are independently alkyl, substituted alkyl, cycloalkyl, substituted cycloalkyl, alkenyl, substituted alkenyl, alkynyl, substituted alkynyl, heteroalkyl, substituted heteroalkyl, heteroalkenyl, substituted heteroalkenyl, aryl, substituted aryl, aryl-($C_1$-$C_3$)alkyl, heterocyclyl, substituted heterocyclyl, heteroaryl, or substituted heteroaryl. The method further comprises the step of exposing at least a portion of the first composition to electromagnetic radiation with a given wavelength at a given intensity for a given period of time, whereby the at least one Cu(II) salt is reduced to a Cu(I) species to a given extent, to generate a second composition. The method further comprises the step of isolating the compound of formula (I) from the second composition.

In one embodiment, the molar ratio of the compound of formula (II) and the compound of formula (III) in the first composition ranges from about 0.5 to about 2. In another embodiment, the at least one reducing agent is a Type (I) photoinitiator. In yet another embodiment, the at least one reducing agent is selected from the group consisting of: 1-hydroxy-cyclohexyl-phenyl-ketone; benzophenone; 2-hydroxy-2-methyl-1-phenyl-1-propanone; 2-hydroxy-1-[4-(2-hydroxyethoxy)phenyl]-2-methyl-1-propanone; methyl benzoylformate; oxy-phenyl-acetic acid 2-[2-oxo-2-phenyl-acetoxy-ethoxy]-ethyl ester; oxy-phenyl-acetic 2-[2-hydroxy-ethoxy]-ethyl ester; oxy-phenyl-acetic acid 2-[2-oxo-2-phenyl-acetoxy-ethoxy]-ethyl ester; alpha,alpha-dimethoxy-alpha-phenylacetophenone; 2-benzyl-2-(dimethylamino)-1-[4-(4-morpholinyl) phenyl]-1-butanone; 2-methyl-1-[4-(methylthio)phenyl]-2-(4-morpholinyl)-1-propanone; diphenyl (2,4,6-trimethylbenzoyl)-phosphine oxide; bis-(eta 5-2,4-cyclopentadien-1-yl)-bis-[2,6-difluoro-3-(1H-pyrrol-1-yl)-phenyl]-titanium; (4-methylphenyl) [4-(2-methylpropyl) phenyl]-iodonium hexafluorophosphate; 2-(4-methylbenzyl)-2-(dimethylamino)-1-(4-morpholinophenyl)-butan-1-one; 4-(2-hydroxyethoxy)phenyl-(2-hydroxy-2-propyl)-ketone; bis-(2,6-dimethoxybenzoyl)-2,4,4-trimethylpentyl phosphine oxide; titanium dioxide; and mixtures thereof. In yet another embodiment, the electromagnetic radiation comprises ultraviolet or visible electromagnetic radiation.

The invention also includes a method of immobilizing a chemical structure in a given pattern onto a section of the surface of a substrate. The method comprises the step of (i) providing the substrate, wherein at least a portion of the surface of the substrate is derivatized with a given compound, wherein the given compound comprises at least one reactive alkynyl group or at least one reactive azide group. The method further comprises the step of (ii) applying a first solution to the surface of the substrate, to generate a first system, wherein: the first solution comprises an alkyne-based substrate if the substrate was derivatized with a compound comprising at least one reactive azide group in step (i), an azide-based substrate if the substrate was derivatized with a compound comprising at least one reactive alkyne group in step (i), at least one Cu(II) salt and at least one photoinducible reducing agent; the alkyne-based substrate comprises at least one reactive alkynyl group; and, the azide-based substrate comprises at least one reactive azide group. The method further comprises the step of (iii) covering the substrate with a photomask and exposing the substrate to electromagnetic radiation with a given wavelength at a given intensity for a given period of time, wherein the transparent portion of the photomask corresponds to the given pattern, whereby the at least one Cu(II) salt is reduced to a Cu(I) species to a given extent, and whereby the chemical structure is formed. The method further comprises the step of (iv) removing any non-immobilized material from the surface of the substrate, wherein the chemical structure is immobilized onto the section in the given pattern.

In one embodiment, in step (ii) the first solution is applied onto the substrate by spin coating. In another embodiment, the at least one reducing agent is a Type (I) photoinitiator. In yet another embodiment, the at least one reducing agent is selected from the group consisting of: 1-hydroxy-cyclohexyl-phenyl-ketone; benzophenone; 2-hydroxy-2-methyl-1-phenyl-1-propanone; 2-hydroxy-1-[4-(2-hydroxyethoxy)phenyl]-2-methyl-1-propanone; methyl benzoylformate; oxy-phenyl-acetic acid 2-[2-oxo-2-phenyl-acetoxy-ethoxy]-ethyl ester; oxy-phenyl-acetic 2-[2-hydroxy-ethoxy]-ethyl ester; oxy-phenyl-acetic acid 2-[2-oxo-2-phenyl-acetoxy-ethoxy]-ethyl ester; alpha,alpha-dimethoxy-alpha-phenylacetophenone; 2-benzyl-2-(dimethylamino)-1-[4-(4-morpholinyl) phenyl]-1-butanone; 2-methyl-1-[4-(methylthio)phenyl]-2-(4-morpholinyl)-1-propanone; diphenyl (2,4,6-trimethylbenzoyl)-phosphine oxide; bis-(eta 5-2,4-cyclopentadien-1-yl)-bis-[2,6-difluoro-3-(1H-pyrrol-1-yl)- phenyl]-titanium; (4-methylphenyl) [4-(2-methylpropyl)phenyl]-iodonium hexafluorophosphate; 2-(4-methylbenzyl)-2-(dimethylamino)-1-(4-morpholinophenyl)-butan-1-one; 4-(2-hydroxyethoxy)phenyl-(2-hydroxy-2-propyl)-ketone; bis-(2,6-dimethoxybenzoyl)-2,4,4-trimethylpentyl phosphine oxide; titanium dioxide; nd mixtures thereof. In yet another embodiment, the electromagnetic radiation comprises ultraviolet or visible electromagnetic radiation.

The invention also includes a method of patterning a chemical structure in a given pattern onto a section of the surface of a substrate. The method includes the step of (i) providing the substrate, wherein at least a portion of the surface of the substrate is derivatized with a given compound; wherein the given compound comprises at least one reactive alkynyl group or at least one reactive azide group. The method further includes the step of (ii) applying a first solution to at least a portion of the surface of the substrate, to generate a first system, wherein the first solution comprises: an alkyne-based substrate comprising at least one reactive alkynyl group, if the given compound in step (i) comprises a reactive azide group; an azide-based substrate comprising at least one reactive azide group, if the given compound in step (ii) comprises a reactive alkynyl group; at least one Cu(II) salt; and, at least one photoinducible reducing agent. The method further includes the step of (iii) covering the substrate with a photomask and exposing the substrate to electromagnetic radiation with a given wavelength at a given intensity for a given period of time, wherein the transparent portion of the photomask corresponds to the given pattern, whereby the at least one Cu(II) salt is reduced to a Cu(I) species to a given extent, and whereby the chemical structure is formed. The method further includes the step of (iv) removing any non-immobilized material from the surface of the substrate, wherein the chemical structure is immobilized onto the section in the given pattern.

In one embodiment, in step (ii) the first solution is applied onto the section by spin coating. In another embodiment, the at least one reducing agent is a Type (I) photoinitiator. In yet another embodiment, the electromagnetic radiation comprises ultraviolet or visible electromagnetic radiation.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising As illustrated in FIG. 1A, the copper catalyzed azide-alkyne reaction is shown to occur in three steps. The alkyne (a) reacts with Cu(I) to form the copper-acetylide (b). This species then reacts with the azide (c) to form the cycloaddition product (d). The catalytic cycle is completed when Cu(I) is regenerated and the triazole product (e) formed. In the radical mediated process Cu(I) is generated by reduction of Cu(II) (reaction R1). Once generated, Cu(I) can potentially disproportionate into Cu(II) and Cu(0) (reaction D), or it could be expected to be further reduced to copper metal by radical reaction (reaction R2). Any ligands present are omitted for clarity. FIG. 1B illustrates a initiation scheme for the photoinduced CuAAC reaction. FIG. 1C illustrates the structures of 1-hexyne (1), ethyl azidoacetate (2), and Irgacure 819 (3), used in the $^1$H-NMR and FTIR experiments, and a 3K PEG-dialkyne (4), a 10K PEG-tetraazide (5) and Irgacure 2959 (6) were used for hydrogel synthesis.

FIG. 9, comprising FIG. 9A: Reaction of 1-dodecyne (concentration as labeled); 200 mM ethylazidoacetate; 10 mM copper (II) sulfate; 10 mM I819; and 20 mW/cm$^2$ irradiation. FIG. 9B: Reaction of 200 mM 1-dodecyne; ethylazidoacetate (concentration as labeled); 10 mM copper (II) sulfate; 10 mM I819; and 20 mW/cm$^2$ irradiation, FIG. 9C: Reaction of 200 mM 1-dodecyne; 200 mM ethylazidoacetate; copper (II) sulfate (concentration as labeled); 10 mM I819; and 20 mW/cm$^2$ irradiation. FIG. 9D: Reaction of 200 mM 1-dodecyne; 200 mM ethylazidoacetate; 10 mM copper (II) sulfate; I819 (concentration as labeled); and 20 mW/cm$^2$ irradiation. FIG. 9E: Reaction of 200 mM 1-dodecyne; 200 mM ethylazidoacetate; 10 mM copper (II) sulfate; 10 mM I819; and irradiation at labeled intensity.

DETAILED DESCRIPTION OF THE INVENTION

Figure 1A:
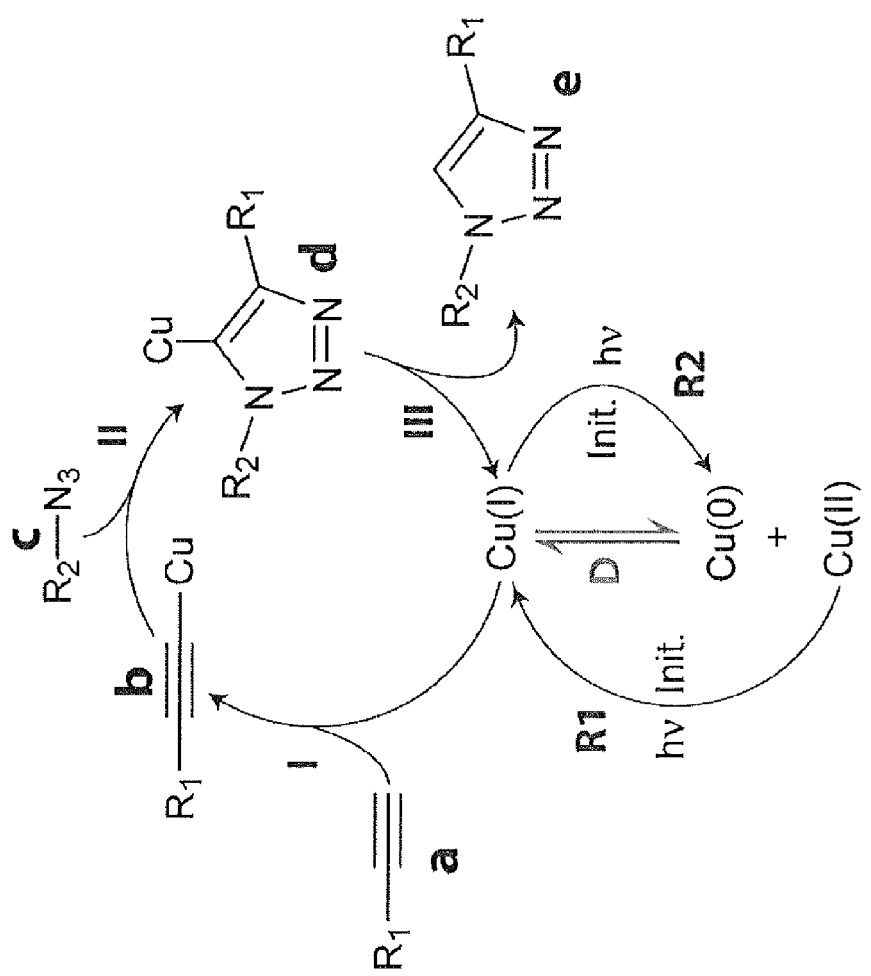
FIGS. 1A-1C, illustrates the chemistry of a photocatalysed CuAAC reaction.

The present invention relates to the unexpected discovery that light irradiation may be used to trigger the copper-catalyzed azide-alkyne cycloaddition (CuAAC) reaction. This development allows full spatial and temporal control of this reaction for the first time, using photolithographic techniques.

In one aspect, CuAAC reactions may be photoinduced by irradiating a system comprising an alkyne-based substrate, an azide-based substrate, a Cu(II) salt and a photoinducible reducing agent, whereby irradiation of the system generates at least one reducing agent that interacts with the Cu(II) salt to locally generate a Cu(I) species. The Cu(I) species catalyzes the CuAAC reaction, wherein the reaction is limited to the area irradiated and its extent is defined by the time of exposure. In a preferred embodiment, the photoinducible reducing agent is a Type (I) photoinitiator.

Temporal control enables one to initiate a reaction on demand, as is critical when materials must be spin coated or mixed before the reaction actually occurs. The ability to spatially and temporally control the CuAAC reaction extends the capabilities of this Click reaction, increasing the number of materials that may be readily patterned through the use of this reaction.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and organic chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a concentration, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "alkyne-based substrate" refers to a small molecule or a polymeric molecule comprising at least one reactive alkynyl group. An "alkynyl group" is an unsaturated, linear or branched or cyclic hydrocarbon group consisting at least one carbon-carbon triple bond. In one embodiment, the alkyne-based substrate comprises preferably at least one terminal alkynyl group (—C≡CH).

As used herein, the term "azide-based substrate" refers to a small molecule or a polymeric molecule comprising at least one azide group. The substrate contemplated within the invention may comprise a soluble reagent or a solid-immobilized reagent, such as a surface-immobilized reagent.

As used herein, the term "photoinducible reducing agent" refers to a molecule that generates at least one reducing species upon irradiation of the reducing agent for a given period of time. In one embodiment, the electromagnetic irradiation comprises ultraviolet, visible or infrared electromagnetic radiation. In another embodiment, the at least one reducing agent is capable of reducing a Cu(II) salt to a Cu(I) species to a given extent, in the given period of time used in the irradiation of the reducing agent. In a non-limiting embodiment, the given extent is calculated as the ratio between (i) the amount of the Cu(II) salt in the system that was reduced to a Cu(I) species and (ii) the amount of the Cu(II) salt in the system before reduction.

As used herein, the term "Type (I) photoinitiator" refers to a compound that undergoes a unimolecular bond cleavage upon irradiation to yield free radicals. Non-limiting examples of Type (I) photoinitiators are benzoin ethers, benzyl ketals, α-dialkoxy-acetophenones, α-hydroxy-alkylphenones, α-amino-alkylphenones and acyl-phosphine oxides. As used herein, the term "Type (II) photoinitiator" refers to a combination of compounds that undergo a bimolecular reaction where the excited state of the photoinitiator interacts with a second molecule (often known as "co-initiator") to generate free radicals.

As used herein, the term "reactive" as applied to azide or alkyne groups indicate that these groups under appropriate conditions may take part in one or more reactions as defined in this application.

As used herein, the term "alkyl," by itself or as part of another substituent means, unless otherwise stated, a straight or branched chain hydrocarbon having the number of carbon atoms designated (i.e. $C_1$-$C_{10}$ means one to ten carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "cycloalkyl," by itself or as part of another substituent means, unless otherwise stated, a cyclic chain hydrocarbon having the number of carbon atoms designated (i.e. $C_3$-$C_6$ means a cyclic group comprising a ring group consisting of three to six carbon atoms) and includes straight, branched chain or cyclic substituent groups, Examples include cyclopropyl, cyclobutyl, cyclopentyl, cyclohexyl, cycloheptyl, and cyclooctyl. Most preferred is ($C_3$-$C_6$) cycloalkyl, particularly cyclopropyl, cyclobutyl, cyclopentyl and cyclohexyl.

As used herein, the term "alkenyl," employed alone or in combination with other terms, means, unless otherwise stated, a stable mono-unsaturated or di-unsaturated straight chain or branched chain hydrocarbon group having the stated number of carbon atoms. Examples include vinyl, propenyl (allyl), crotyl, isopentenyl, butadienyl, 1,3-pentadienyl, 1,4-pentadienyl, and the higher homologs and isomers. A functional group representing an alkene is exemplified by —$CH_2$—CH=$CH_2$.

As used herein, the term "alkynyl," employed alone or in combination with other terms, means, unless otherwise stated, a stable straight chain or branched chain hydrocarbon group with a triple carbon-carbon bond, having the stated number of carbon atoms. Examples include ethynyl and propynyl, and the higher homologs and isomers.

As used herein, the term "substituted alkyl," "substituted cycloalkyl," "substituted alkenyl" or "substituted alkynyl" means alkyl, cycloalkyl, alkenyl or alkynyl, as defined above, substituted by one, two or three substituents selected from the group consisting of halogen, —OH, alkoxy, —$NH_2$, —N($CH_3$)$_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —N($CH_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl, and naphthyl. Preferred are phenyl and naphthyl, most preferred is phenyl.

As used herein, the term "aryl-($C_1$-$C_3$)alkyl" means a functional group wherein a one to three carbon alkylene chain is attached to an aryl group, e.g., —$CH_2CH_2$-phenyl. Preferred is aryl-$CH_2$— and aryl-CH($CH_3$)—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heterocycle" or "heterocyclyl" or "heterocyclic" by itself or as part of another substituent means, unless otherwise stated, an unsubstituted or substituted, stable, mono- or multi-cyclic heterocyclic ring system that consists of carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzothryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

As used herein, the term "instructional material" includes a publication, a recording, a diagram, or any other medium of expression that may be used to communicate the usefulness of the compositions and methods of the invention, In some instances, the instructional material may be part of a kit useful for performing a phtoinduced CuAAC reaction. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; or instructions for use of a composition of the invention.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from Ito 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to the unexpected discovery that CuAAC reactions may be photoinduced by irradiating a system comprising an alkyne-based substrate, an azide-based substrate, a Cu(II) salt and a photochemical reducing agent. Irradiation of the system generates at least one reducing agent, which interacts with the Cu(II) salt to locally generate a Cu(I) species, which catalyzes the CuAAC reaction to form the 1,2,3-triazole. In one embodiment, the photochemical reducing agent is a Type (I) photoinitiator.

Figure 1B:
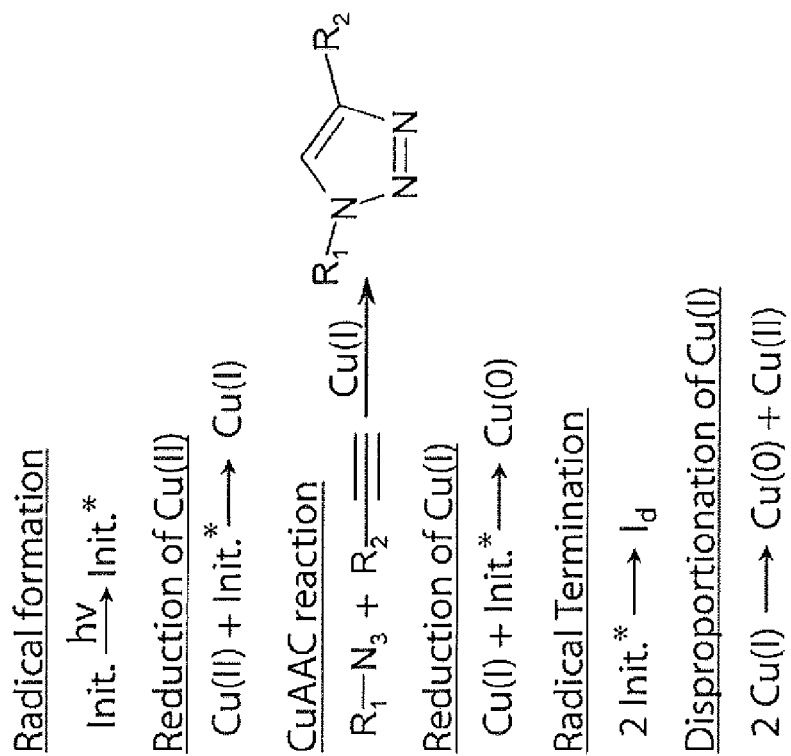
Figure 1C:
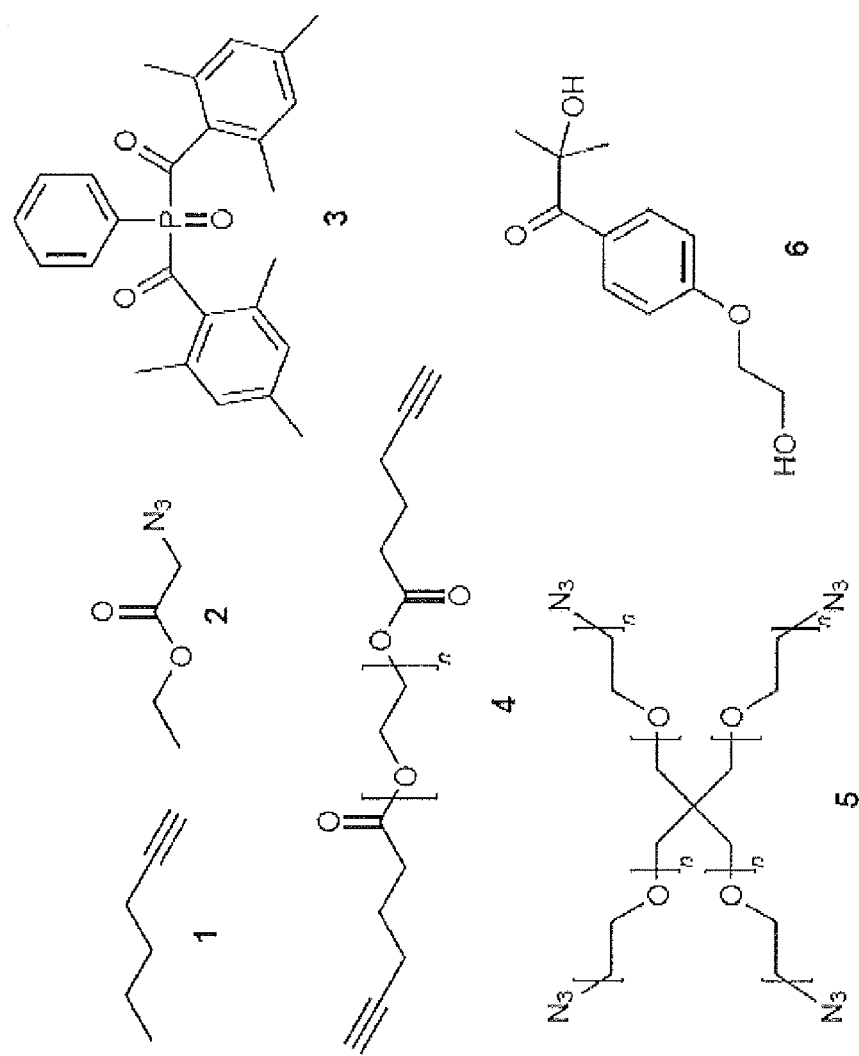

While the 1,3-dipolar azide-alkyne cycloaddition reaction is not influenced by conventional photogenerated active species (such as carbocations and radicals), the reaction rate is increased approximately $10^7$ times by catalytic amounts of Cu(I) (Meldal, 2008, Macromol. Rapid Comm. 29(12-13): 1016). This catalytic behavior permits the photochemical generation of Cu(I) to be utilized in a manner analogous to generation of radical or carbocation species in traditional photopolymerization processes, and enables spatial and temporal control of the CuAAC reaction. As illustrated in FIG. 1, a cleavage-type photoinitiator may be used to generate radicals, which reduce Cu(II) to Cu(I). The transiently generated Cu(I) catalyzes the 1,3-dipolar cycloaddition, enabling a photoinducible azide-alkyne cycloaddition (pCuAAC) reaction before possibly being reduced to Cu(0). Disproportionation is another potential fate for Cu(I) and radicals.

Compositions of the Invention

In one aspect, the invention includes a composition comprising an alkyne-based substrate, an azide-based substrate, at least one Cu(II) salt and at least one photoinducible reducing agent. In one embodiment, the alkyne-based substrate is attached to a hydrogel. In another embodiment, the azide-based substrate is attached to a hydrogel. In another embodiment, the at least one photoinducible reducing agent is a Type (I) photoinitiator.

The alkyne-based substrate contemplated within the invention is a small molecule or a polymeric molecule comprising at least one reactive alkynyl group. In one embodiment, the alkyne-based substrate comprises at least one terminal alkynyl group.

The azide-based substrate contemplated within the invention is a small molecule or a polymeric molecule comprising at least one reactive azide group.

In one embodiment, the molar ratio of the at least one reactive alkyne group and the at least one reactive azide group in the composition ranges from about $10^{-10}$ to about $10^{+10}$. In another embodiment, the molar ratio of the at least one reactive alkyne group and the at least one reactive azide group in the composition ranges from about $10^{-8}$ to about $10^{+8}$. In another embodiment, the molar ratio of the at least one reactive alkyne group and the at least one reactive azide group in the composition ranges from about $10^{-6}$ to about $10^{+6}$. In another embodiment, the molar ratio of the at least one reactive alkyne group and the at least one reactive azide group in the composition ranges from about $10^{-4}$ to about $10^{+4}$. In another embodiment, the molar ratio of the at least one reactive alkyne group and the at least one reactive azide group in the composition ranges from about $10^{-3}$ to about $10^{+3}$. In another embodiment, the molar ratio of the at least one reactive alkyne group and the at least one reactive azide group in the composition ranges from about $10^{-2}$ to about $10^{+2}$. In another embodiment, the molar ratio of the at least one reactive alkyne group and the at least one reactive azide group in the composition ranges from about $10^{-1}$ to about 10. In yet another embodiment, the molar ratio of the at least one reactive alkyne group and the at least one reactive azide group in the composition ranges from about 0.5 to about 2. In yet another embodiment, the molar ratio of the at least one reactive alkyne group and the at least one reactive azide group in the composition ranges from about 0.5 to about 0.75. In another embodiment, the molar ratio of the at least one reactive alkyne group and the at least one reactive azide group in the composition ranges from about 0.75 to about 0.85. In yet another embodiment, the molar ratio of the at least one reactive alkyne group and the at least one reactive azide group in the composition ranges from about 0.85 to about 1. In yet another embodiment, the molar ratio of the at least one reactive alkyne group and the at least one reactive azide group in the composition is about 1. In yet another embodiment, the molar ratio of the at least one reactive alkyne group and the at least one reactive azide group in the composition ranges from about 1 to about 1.15. In yet another embodiment, the molar ratio of the at least one reactive alkyne group and the at least one reactive azide group in the composition ranges from about 1.15 to about 1.25. In yet another embodiment, the molar ratio of the at least one reactive alkyne group and the at least one reactive azide group in the composition ranges from about 1.25 to about 1.5.

The at least one Cu(II) salt contemplated within the invention comprises a copper(II)-containing salt, such as, but not limited to, copper(II) sulfate, copper(II) chloride, copper(II) bromide, copper(II) iodide, copper(II) perchlorate, copper(II) nitrate, copper(II) hydroxide, copper(II) oxide, and hydrates and mixtures thereof. Non-limiting examples of hydrates are copper(II) sulfate pentahydrate, copper(II) nitrate hydrate, copper(II) nitrate.2.5H$_2$O, copper(II) perchlorate hexahydrate, copper(II) chloride dihydrate and the like.

The at least one photoinducible reducing agent contemplated within the invention is a molecule that generates at least one reducing species upon irradiation of the reducing agent with a given wavelength at a given intensity for a given period of time. A radical photoinitiator known in the art may be employed, such as benzoin ethers and phenone derivatives such as benzophenone or diethoxyacetophenone. In one embodiment, the irradiation comprises ultraviolet electromagnetic radiation (wavelength from about 10 nm to about 400 nm), visible electromagnetic radiation (wavelength from about 400 nm to about 750 nm) or infrared electromagnetic radiation (radiation wavelength from about 750 nm to about 300,000 nm). In another embodiment, the electromagnetic radiation comprises ultraviolet or visible electromagnetic radiation.

Ultraviolet or UV light as described herein includes UVA light, which generally has wavelengths between about 320 and about 400 nm, UVB light, which generally has wavelengths between about 290 nm and about 320 nm, and UVC light, which generally has wavelengths between about 200 nm and about 290 nm. UV light may include UVA, UVB, or UVC light alone or in combination with other type of UV light. In one embodiment, the UV light source emits light between about 350 nm and about 400 nm. In some embodiments, the UV light source emits light between about 400 nm and about 500 nm.

In one embodiment, the at least one reducing agent is capable of reducing the at least one Cu(II) salt of the composition to a given extent to a Cu(I) species, upon irradiation of the composition for the given period of time. In another embodiment, the given extent is from about 0.01% to about 5%. In yet another embodiment, the given extent is from about 5% to about 10%. In yet another embodiment, the given extent is from about 10% to about 25%. In yet another embodiment, the given extent is from about 25% to about 50%. In yet another embodiment, the given extent is from about 50% to about 75%. In another embodiment, the given extent is from about 75% to about 100%.

Non-limiting examples of the at least one reducing agent contemplated within the invention are:

1-hydroxy-cyclohexyl-phenyl-ketone (Irgacure 184; Ciba, Hawthorne, N.J.);
a 1:1 mixture of 1-hydroxy-cyclohexyl-phenyl-ketone and benzophenone (Irgacure 500; Ciba, Hawthorne, N.J.);
2-hydroxy-2-methyl-1-phenyl-1-propanone (Darocur™ 1173; Ciba, Hawthorne, N.J.);
2-hydroxy-1-[4-(2-hydroxyethoxy)phenyl]-2-methyl-1-propanone (Irgacure 2959; Ciba, Hawthorne, N.J.);
methyl benzoylformate (Darocur™ MBF; Ciba, Hawthorne, N.J.);
oxy-phenyl-acetic acid 2-[2-oxo-2-phenyl-acetoxy-ethoxy]-ethyl ester;
oxy-phenyl-acetic 2-[2-hydroxy-ethoxy]-ethyl ester;
a mixture of oxy-phenyl-acetic acid 2-[2-oxo-2-phenyl-acetoxy-ethoxy]-ethyl ester and oxy-phenyl-acetic 2-[2-hydroxy-ethoxy]-ethyl ester (Irgacure 754; Ciba, Hawthorne, N.J.);
alpha,alpha-dimethoxy-alpha-phenylacetophenone (Irgacure 651; Ciba, Hawthorne, N.J.);
2-benzyl-2-(dimethylamino)-1-[4-(4-morphanyl)-phenyl]-1-butanone (Irgacure 369; Ciba, Hawthorne, N.J.);
2-methyl-1-[4-(methylthio)phenyl]-2-(4-morpholinyl)-1-propanone (Irgacure 907; Ciba, Hawthorne, N.J.);
a 3:7 mixture of 2-benzyl-2-(dimethylamino)-1-[4-(4-morpholinyl) phenyl]-1-butanone and alpha,alpha-dimethoxy-alpha-phenylacetophenone per weight (Irgacure 1300; Ciba, Hawthorne, N.J.);
diphenyl-(2,4,6-trimethylbenzoyl) phosphine oxide (Darocur™ TPO; Ciba, Hawthorne, N.J.);
a 1:1 mixture of diphenyl-(2,4,6-trimethylbenzoyl)-phosphine oxide and 2-hydroxy-2-methyl-1-phenyl-1-propanone (Darocur™ 4265; Ciba, Hawthorne, N.J.);
phenyl bis(2,4,6-trimethyl benzoyl) phosphine oxide, which may be used in pure form (Irgacure 819; Ciba, Hawthorne, N.J.) or dispersed in water (45% active, Irgacure 819DW; Ciba, Hawthorne, N.J.);
a 2:8 mixture of phosphine oxide, phenyl bis(2,4,6-trimethyl benzoyl) and 2-hydroxy-2-methyl-1-phenyl-1-propanone (Irgacure 2022; Ciba, Hawthorne, N.J.);
Irgacure 2100, which comprises phenyl-bis(2,4,6-trimethyl-benzoyl)-phosphine oxide);
bis-(eta 5-2,4-cyclopentadien-1-yl)-bis-[2,6-difluoro-3-(1H-pyrrol-1-yl) phenyl]-titanium (Irgacure 784; Ciba, Hawthorne, N.J.);
(4-methylphenyl) [4-(2-methylpropyl) phenyl]-iodonium hexafluorophosphate (Irgacure 250; Ciba, Hawthorne, N.J.);
2-(4-methylbenzyl)-2-(dimethylamino)-1-(4-morpholinophenyl)-butan-1-one (Irgacure 379; Ciba, Hawthorne, N.J.);
4-(2-hydroxyethoxy)phenyl-(2-hydroxy-2-propyl)ketone (Irgacure 2959; Ciba, Hawthorne, N.J.);
bis-(2,6-dimethoxybenzoyl)-2,4,4-trimethylpentylphosphine oxide;
a mixture of bis-(2,6-dimethoxybenzoyl)-2,4,4-trimethylpentylphosphine oxide and 2-hydroxy-2-methyl-1-phenyl-propanone. (Irgacure 1700; Ciba, Hawthorne, N.J.);
titanium dioxide;
and mixtures thereof.

The at least one reducing agent may be used in amounts ranging from about 0.01 to about 25 weight percent (wt %) of the composition, more preferably from about 0.1 to about 20 weight percent (wt %) of the composition, more preferably from about 1 to about 15 weight percent (wt %) of the composition, more preferably from about 2 to about 10 weight percent (wt %) of the composition.

The at least one Cu(II) salt may be used in amounts in which the ranging from about 0.01 to about 25 weight percent (wt %) of the composition, more preferably from about 0.1 to about 20 weight percent (wt %) of the composition, more preferably from about I to about 15 weight percent (wt %) of the composition, more preferably from about 2 to about 10 weight percent (wt %) of the composition.

Methods of the Invention

In one aspect, the invention includes a method of preparing a compound of formula (I):

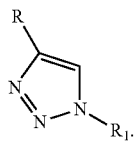
(I)

The method comprises the steps of:
(i) mixing a compound of formula (II):

(II)

a compound of formula (III):

(III), at least one Cu(II) salt and at least one photoinducible reducing agent, to generate a first composition, wherein R and $R_1$ are independently alkyl, substituted alkyl, cycloalkyl, substituted cycloalkyl, alkenyl, substituted alkenyl, alkynyl, substituted alkynyl, heteroalkyl, substituted heteroalkyl, heteroalkenyl, substituted heteroalkenyl, awl, substituted aryl, aryl-$(C_1-C_3)$alkyl, heterocyclyl, substituted heterocyclyl, heteroaryl, or substituted heteroaryl; (ii) exposing at least a portion of the first composition to electromagnetic radiation with a given wavelength at a given intensity for a given period of time, whereby the at least one Cu(II) salt is reduced to a Cu(I) species to a given extent, to generate a second composition;

and, (iii) isolating the compound of formula (I) from the second composition.

In one embodiment, the molar ratio of the compound of formula (II) and the compound of formula (III) in the first composition ranges from about 0.5 to about 2.

In one embodiment, the at least one Cu(II) salt is selected from the group consisting of copper(II) sulfate, copper(II) chloride, copper(II) bromide, copper(II) iodide, copper(II) perchlorate, copper(II) nitrate, copper(II) hydroxide, copper (II) oxide, copper(II) sulfate pentahydrate, copper(II) nitrate hydrate, copper(II) nitrate.2.5H$_2$O, copper(II) perchlorate hexahydrate, copper(II) chloride dehydrate, and mixtures thereof.

In one embodiment, the at least one photoinducible reducing agent is a Type (I) photoinitiator. In another embodiment, the at least one reducing agent is selected from the group consisting of: 1-hydroxy-cyclohexyl-phenyl-ketone; benzophenone; 2-hydroxy-2-methyl-1-phenyl-1-propanone; 2-hydroxy-1-[4-(2-hydroxyethoxy)phenyl]-2-methyl-1-propanone; methyl benzoylformate; oxy-phenyl-acetic acid 2-[2-oxo-2-phenyl-acetoxy-ethoxy]-ethyl ester; oxy-phenyl-acetic 2-[2-hydroxy-ethoxy]-ethyl ester; oxy-phenyl-acetic acid 2-[2-oxo-2-phenyl-acetoxy-ethoxy]-ethyl ester; alpha,alpha-dimethoxy-alpha-phenylacetophenone; 2-benzyl-2-(dimethylamino)-1-[4-(4-morpholinyl)phenyl]-1-butan one; 2-methyl-1-[4-(methylthio)phenyl]-2-(4-morpholinyl)-1-propanone; diphenyl (2,4,6-trimethylbenzoyl)-phosphine oxide; bis-(eta 5-2,4-cyclopentadien-1-yl)-bis-[2,6-difluoro-3-(1H-pyrrol-1-yl)-phenyl]-titanium; (4-methylphenyl) [4-(2-methylpropyl) phenyl]-iodonium hexafluorophosphate; 2-(4-methylbenzyl)-2-(dimethylamino)-1-(4-morpholinophenyl)-butan-1-one; 4-(2-hydroxyethoxy)phenyl-(2-hydroxy-2-propyl)-ketone; bis-(2,6-dimethoxybenzoyl)-2,4,4-trimethylpentyl phosphine oxide; titanium dioxide; and mixtures thereof.

In one embodiment, the at least one reducing agent ranges from about 0.01% to about 25% weight of the first composition. In another embodiment, the at least one Cu(II) salt ranges from about 0.01% to about 25% weight of the first composition. In yet another embodiment, the electromagnetic radiation comprises ultraviolet or visible electromagnetic radiation.

In another aspect, the invention comprises a method of immobilizing a chemical structure in a given pattern onto a section of the surface of a substrate. The method comprises the step of (i) providing the substrate, wherein at least a portion of the surface of the substrate is derivatized with a given compound, wherein the given compound comprises at least one reactive alkynyl group or at least one reactive azide group. The method further comprises the step of (ii) applying a first solution to the surface of the substrate, to generate a first system. The first solution comprises an alkyne-based substrate if the substrate was derivatized with a compound comprising at least one reactive azide group in step (i), an azide-based substrate if the substrate was derivatized with a compound comprising at least one reactive alkyne group in step (i), at least one Cu(II) salt and at least one photoinducible reducing agent. In one embodiment, the alkyne-based substrate comprises at least one reactive alkynyl group. In another embodiment, the azide-based substrate comprises at least one reactive azide group. The method further comprises the step of (iii) covering the substrate with a photomask and exposing the substrate to electromagnetic radiation with a given wavelength at a given intensity for a given period of time, wherein the transparent portion of the photomask corresponds to the given pattern, whereby the at least one Cu(II) salt is reduced to a Cu(I) species to a given extent, and whereby the chemical structure is formed. The method further comprises the step of (iv) removing any non-immobilized material from the surface of the substrate, wherein the chemical structure is immobilized onto the section in the given pattern.

In one embodiment, in step (ii) the first solution is applied onto the substrate by spin coating. In another embodiment, the at least one Cu(II) salt is selected from the group consisting of copper(II) sulfate, copper(II) chloride, copper(II) bromide, copper(II) iodide, copper(II) perchlorate, copper(II) nitrate, copper(II) hydroxide, copper(II) oxide, copper(II) sulfate pentahydrate, copper(II) nitrate hydrate, copper(II) nitrate.2.5H$_2$O, copper(II) perchlorate hexahydrate, copper(II) chloride dehydrate, and mixtures thereof. In yet another embodiment, the at least one reducing agent is a Type (I) photoinitiator. In yet another embodiment, the at least one reducing agent is selected from the group consisting of 1-hydroxy-cyclohexyl-phenyl-ketone; benzophenone; 2-hydroxy-2-methyl-1-phenyl-1-propanone; 2-hydroxy-1-[4-(2- hydroxyethoxy)phenyl]-2-methyl-1-propanone; methyl benzoylformate; oxy-phenyl-acetic acid 2-[2-oxo-2-phenyl-acetoxy-ethoxy]-ethyl ester; oxy-phenyl-acetic 2-[2-hydroxy-ethoxy]-ethyl ester; oxy-phenyl-acetic acid 2-[2-oxo-2-phenyl-acetoxy-ethoxy]-ethyl ester; alpha,alpha-dimethoxy-alpha-phenylacetophenone; 2-benzyl-2-(dimethylamino)-1-[4-(4-morpholinyl) phenyl]-1-butanone; 2-methyl-1-[4-(methylthio)phenyl]-2-(4-morpholinyl)-1-propanone; diphenyl (2,4,6-trimethylbenzoyl)-phosphine oxide; bis-(eta 5-2,4-cyclopentadien-1-yl)-bis-[2,6-difluoro-3-(1H-pyrrol-1-yl)-phenyl]-titanium; (4-methylphenyl) [4-(2-methylpropyl)phenyl]-iodonium hexafluorophosphate; 2-(4-methylbenzyl)-2-(dimethylamino)-1-(4-morpholinophenyl)-butan-1-one; 4-(2-hydroxyethoxy)phenyl-(2-hydroxy-2-propyl)-ketone; bis-(2,6-dimethoxybenzoyl)-2,4,4-trimethylpentyl phosphine oxide; titanium dioxide; and mixtures thereof.

In one embodiment, the at least one reducing agent ranges from about 0.01% to about 25% weight of the first solution. In another embodiment, the at least one Cu(II) salt ranges from about 0.01% to about 25% weight of the first solution. In yet one embodiment, the electromagnetic radiation comprises ultraviolet or visible electromagnetic radiation.

In yet another aspect, the invention includes a method of patterning a chemical structure in a given pattern onto a section of the surface of a substrate. The method comprises the step of (i) providing the substrate, wherein at least a portion of the surface of the substrate is derivatized with a given compound; wherein the given compound comprises at least one reactive alkynyl group or at least one reactive azide group. The method further comprises the step of (ii) applying a first solution to at least a portion of the surface of the substrate, to generate a first system. The first solution comprises: an alkyne-based substrate comprising at least one reactive alkynyl group if the given compound in step (i) comprises a reactive azide group; an azide-based substrate comprising at least one reactive azide group if the given compound in step (i) comprises a reactive alkynyl group; at least one Cu(II) salt; and, at least one photoinducible reducing agent. The method further comprises the step of (iii) covering the substrate with a photomask and exposing the substrate to electromagnetic radiation with a given wavelength at a given intensity for a given period of time, wherein the transparent portion of the photomask corresponds to the given pattern, whereby the at least one Cu(II) salt is reduced to a Cu(I) species to a given extent, and whereby the chemical structure is formed. The method further comprises the step of (iv) removing any non-immobilized material from the surface of the substrate, wherein the chemical structure is immobilized onto the section in the given pattern.

In one embodiment, in step (ii) the first solution is spin coated onto the section. In another embodiment, the at least one Cu(II) salt is selected from the group consisting of copper (II) sulfate, copper(II) chloride, copper(II) bromide, copper (II) iodide, copper(II) perchlorate, copper(II) nitrate, copper (II) hydroxide, copper(II) oxide, copper(II) sulfate pentahydrate, copper(II) nitrate hydrate, copper(II) nitrate.2.5H$_2$O, copper(II) perchlorate hexahydrate, copper (II) chloride dehydrate, and mixtures thereof. In yet another embodiment, the at least one reducing agent is selected from the group consisting of 1-hydroxy-cyclohexyl-phenyl-ketone; benzophenone; 2-hydroxy-2-methyl-1-phenyl-1-propanone; 2-hydroxy-1-[4-(2-hydroxyethoxy)phenyl]-2-methyl-1-propanone; methyl benzoylformate; oxy-phenyl-acetic acid 2-[2-oxo-2-phenyl-acetoxy-ethoxy]-ethyl ester; oxy-phenyl-acetic 2-[2-hydroxy-ethoxy]-ethyl ester; oxy-phenyl-acetic acid 2-[2-oxo-2-phenyl-acetoxy-ethoxy]-ethyl ester; alpha,alpha-dimethoxy-alpha-phenylacetophenone; 2-benzyl-2-(dimethylamino)-1-[4-(4-morpholinyl)phenyl]-1-butanone; 2-methyl-1-[4-(methylthio)phenyl]-2-(4-morpholinyl)-1-propanone; diphenyl (2,4,6-trimethylbenzoyl)-phosphine oxide; bis-(eta 5-2,4-cyclopentadien-1-yl)-bis-[2,6-difluoro-3-(1H-pyrrol-1-yl)-phenyl]-titanium; (4-methylphenyl) [4-(2-methylpropyl) phenyl]-iodonium hexafluorophosphate; 2-(4-methylbenzyl)-2-(dimethylamino)-1-(4-morpholinophenyl)-butan-1-one; 4-(2-hydroxyethoxy)phenyl-(2-hydroxy-2-propyl)-ketone; bis-(2,6-dimethoxybenzoyl)-2,4,4-trimethylpentyl phosphine oxide; titanium dioxide; and mixtures thereof.

In one embodiment, the at least one reducing agent ranges from about 0.01% to about 25% weight of the first solution. In another embodiment, the at least one Cu(II) salt ranges from about 0.01% to about 25% weight of the first solution. In yet another embodiment, the electromagnetic radiation comprises ultraviolet or visible electromagnetic radiation.

In one embodiment, the azide-based substrate comprises 2-(6-amino-3-imino-4,5-disulfo-3H-xanthen-9-yl)benzoic acid or a salt thereof. In another embodiment, the azide-based substrate comprises 2-(6-amino-3-imino-4,5-disulfo-3H-xanthen-9-yl)-5-(6-azidohexyl)carbamoyl)benzoic acid (Alexa Fluor™ 488 azide or Alexa Fluor™ 4885-carboxamide-(6-azidohexanyl)) or a salt thereof.

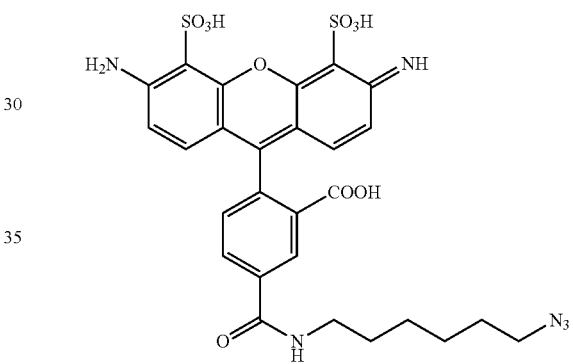

2-(6-amino-3-imino-4,5-disulfo-3H-xanthen-9-yl)-5-(6-azidohexyl)carbamoyl)benzoic acid In one embodiment, the alkyne-based substrate comprises 2-(6-amino-3-imino-4,5-disulfo-3H-xanthen-9-yl)benzoic acid or a salt thereof. In another embodiment, the alkyne-based substrate comprises 2-(6-amino-3-imino-4,5-disulfo-3H-xanthen-9-yl)-5-(prop-2-yn-1-ylcarbamoyl)benzoic acid (Alexa Fluor™ 488 alkyne or a salt thereof.

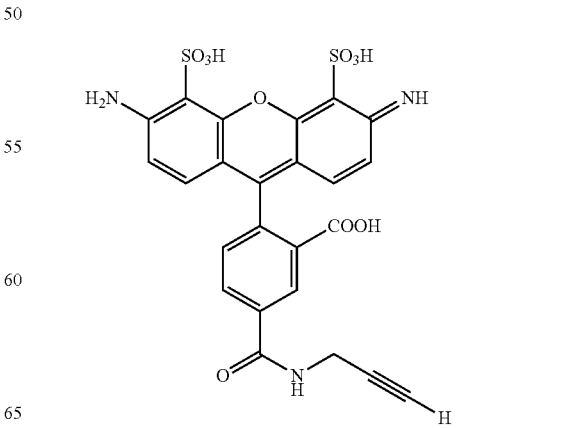

2-(6-amino-3-imino-4,5-disulfo-3H-xanthen-9-yl)-5-(prop-2-yn-1-ylcarbamoyl)benzoic acid Kits of the Invention The invention includes a kit relating to the compositions and methods of the invention. Although exemplary kits are described below, the contents of other useful kits will be apparent to the skilled artisan in light of the present disclosure. Each of these kits is included within the invention. The kits of the present invention are useful, because, as disclosed elsewhere herein, such kits can be used to immobilize a chemical structure in a given pattern onto a section of the surface of a solid substrate. As disclosed elsewhere herein, the methods of the invention may be used to create well-defined patterns on a solid substrate, allowing the selective display of chemical groups on solid surfaces.

The kits of the present invention may be used to immobilize compounds onto a section of the surface of a solid substrate. This is possible by the use to photoinduced Click reactions, which allow spatial and temporal control of the immobilization process.

The kit of the present invention may comprise the reagents necessary to set up a photoinduced Click reaction between an alkyne-based substrate and an azide-based substrate. The kit of the present invention may further comprise components that allow the modification of a solid surface, so that the products of the photoinduced Click reaction are covalently bound to solid surface.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However; they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

The following compounds were used without further purification: 1-hexyne (Sigma Aldrich, St. Louis, Mo.), methanol, dimethylformamide (DMF) (Sigma Aldrich, St. Louis, Mo.), Alexa Fluor 488 5-carboxamide-(6-azidohexanyl), bis(triethylamine salt) 5-isomer (Invitrogen, Carlsbad, Calif.), copper sulfate pentahydrate (Sigma Aldrich, St. Louis, Mo.), Irgacure 819 (bis(2,4,6-trimethylbenzoyl)-phenylphosphineoxide; Ciba, Basel, Switzerland), Irgacure 2959 (1-[4-(2-hydroxyethoxy)-phenyl]-2-hydroxy-2-methyl-1-propane-1-one; Ciba, Basel, Switzerland), and PEG 100K (Polysciences, Warrington, Pa.). PEG 10K tetra-azide was synthesized following previously published procedures (DeForest et al., 2009, Nat. Mat. 8(8):659).

Ethyl azidoacetate (~0.25% in ethanol, Sigma Aldrich) was mixed with dimethylformamide and then reduced in vacuo. The ultimate ethyl azideacetate concentration was determined by $^1$H-NMR.

Synthesis of PEG 3K dialkyne:

4-pentynoic acid (1.64 g, 16.7 mmol, Fluka, St. Louis, Mo.) was added to N,N'-dicyclohexylcarbodiimide (3.44 g, 16.7 mmol, Sigma, St. Louis, Mo.), dissolved in minimal dichloromethane, and stirred overnight under argon. The 4-pentynoic anhydride product was filtered, concentrated, and added to a solution containing vacuum dried poly(ethylene glycol) (5 g, 1.67 mmol, $M_n$~3000; Fluka, St. Louis, Mo.), pyridine (1.34 mL, 16.7 mmol; Sigma, St. Louis, Mo.), 4-dimethylaminopyridine (200 mg, 1.67 mmol; Sigma, St. Louis, Mo.) in minimal dichloromethane, and stirred overnight under argon. The crude product was concentrated, precipitated in diethyl ether, dissolved in deionized water, dialyzed for two days, and lyophilized to give the desired product. $^1$H NMR (CDCl$_3$): δ 1.99 (2H, t, 2×CH$_2$CH$_2$C≡C$\underline{H}$), 2.49-2.61 (8H, m, 2×C$\underline{H_2}$C$\underline{H_2}$C≡CH), 3.60-3.70 (m, OC$\underline{H_2}$C$\underline{H_2}$O), 4.26 (4H, t, 2×OCH$_2$C$\underline{H_2}$° OOC).

Slide Functionalization:

Glass micro slides (Corning) were cleaned using piranha solution, rinsed, and dried thoroughly. Subsequently, they were immersed in a (3-mercaptopropyl)-trimethoxysilane, n-butyl amine, and toluene solution (70 mM of the silane and amine) for approximately 4-12 hours. After rinsing in toluene, the slides were then immersed in a solution of 120 mM propargyl acrylate and 40 mM triethylamine for 4-12 hours.

The contact angle of a pendant water droplet on the surface of the slides functionalized with (3-mercaptopropyl)-trimethoxysilane was found to be 58.3±0.8°. The contact angle of the slides that were further treated with propargyl acrylate was found to be 55.3±1.0°. Gels formed on the surface of both thiol and acrylate functionalized slides were found to adhere to the surface and could only be removed with a razor blade. Gels formed on native glass were easily removed after rinsing with water. This suggested that the gels were covalently bound to the surface via either the CuAAC reaction or radical mediated thiol-alkyne reaction rather than through physical interactions.

Fourier Transform Infrared (FTIR) Spectroscopy:

A Nicolet Magna-IR 750 Series II FTIR spectrometer, outfitted with a horizontal transmission stage, was used in conjunction with a variable path length liquid cell with calcium difluoride windows (International Crystal Laboratories, Garfield, N.J.). A path length of 50 μm was used for all experiments enabling greater than 90% transmission of light. The samples were irradiated by an EXFO Acticure high pressure mercury vapor short arc lamp equipped with a 400-500 nm bandgap filter. Light intensities were measured using an International Light IL1400A radiometer equipped with a GaAsP detector and a quartz diffuser.

Example 1

Photo-CuAAC Reaction of Ethylazide Acetate and 1-Hexyne

Figure 2:
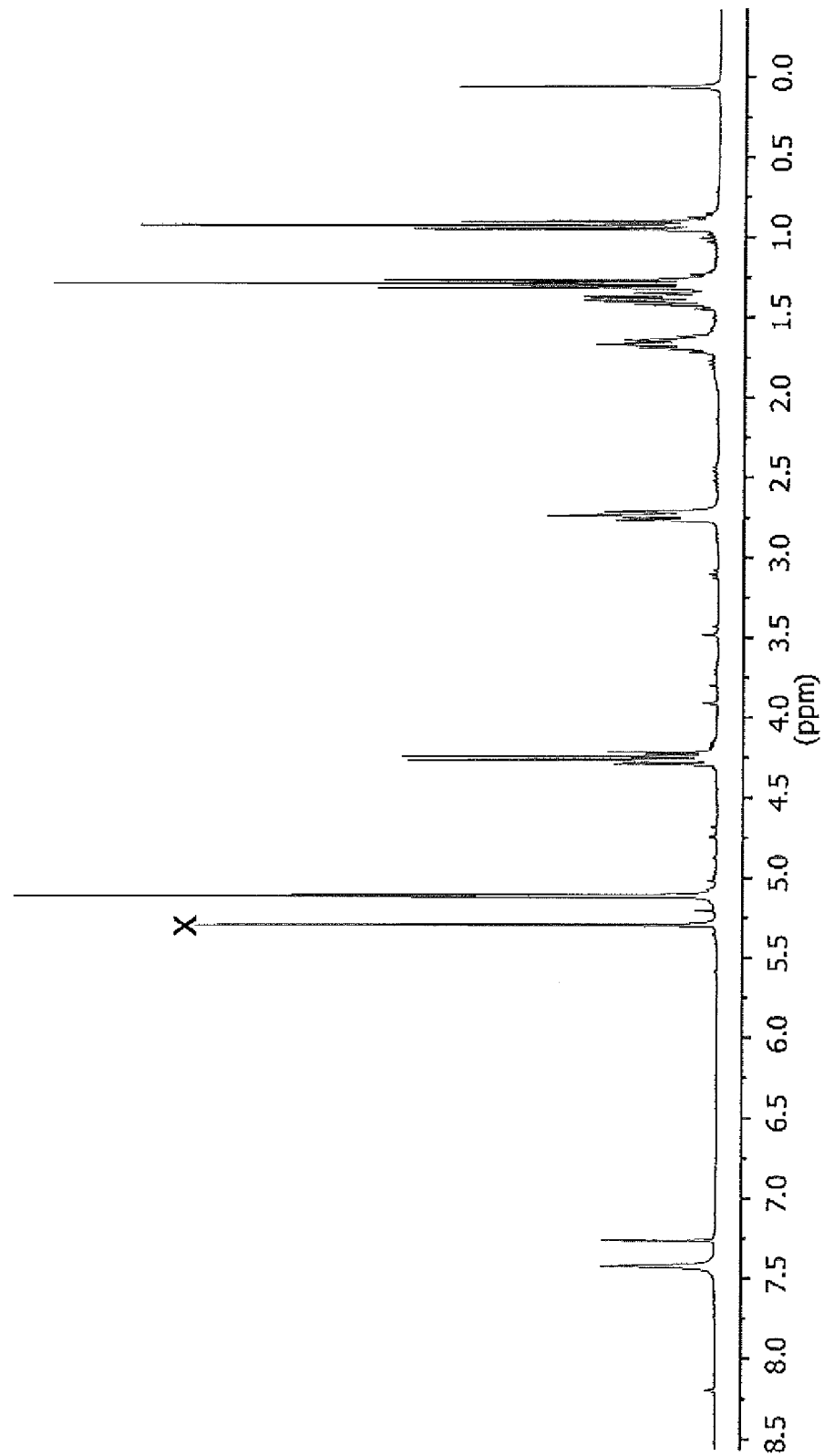
FIG. 2 illustrates the $^1$H NMR spectrum in chloroform-d for the compound prepared in Example 1.

Ethyl azidoacetate (20 mM), 1-hexyne (20 mM), CuSO$_4$ (10 mM), Irgacure 2959 (10 mM), and methanol were combined in a 20 ml scintillation vial and stirred rapidly at room temperature. The sample was then irradiated for 50 minutes using 10 mW/cm$^2$ from an Acticure 4000 lamp using a 365 nm bandgap filter. The resulting mixture was extracted with dichloromethane and 5% aqueous ammonium hydroxide. The organic layer was separated, dried over MgSO$_4$, filtered, and evaporated to give triazole product. $^1$H-NMR (CDCl$_3$): 0.93 (3H t), 1.29 (3H t), 1.42 (2H m), 1.67 (2H m), 2.74 (2H t), 4.25 (2H q), 5.12 (2H s), 7.42 (1H s). The $^1$H NMR spectrum is illustrated in FIG. 2.

In this experiment, UV irradiation of an aqueous solution of monofunctional azide and alkyne species (ethyl azidoacetate and 1-hexyne) in the presence of a photoinitiator and copper (II) sulfate pentahydrate (structures represented in FIG. 1C) generated radicals that subsequently reduced Cu(II) to Cu(I). $^1$H-NMR spectroscopy revealed complete conversion (98% yield) of azide and alkyne functional groups and production of the expected triazole species without side products (FIG. 2). The use of TiO$_2$ as a radical source produced similar results, but due to the heterogeneous nature of TiO$_2$ the system may not be readily amenable to further experimental analysis.

Example 2

Photo-CuAAC Reaction, as Monitored by FTIR Spectroscopy

In one aspect, the performance of the CuAAC reaction may depend strongly on the amplified character of this process, as each photointiated radical leads to a Cu(I) species that subsequently catalyzes many reactions. Kinetic aspects of the reaction were explored by monitoring the concentration of ethylazidoacetate via Fourier transform infrared spectroscopy (FTIR).

In a typical experiment, a solution of dimethylformamide (DMF) with 200 mM ethyl azidoacetate, 200 mM 1-hexyne, 10 mM copper sulfate pentahydrate, and 10 mM Irgacure 819 was injected into the liquid cell. Irgacure 819 was selected as the photosensitive radical generator due to its absorbance at 405 nm, Irradiation was commenced between 5 and 10 minutes. Approximately 1.8 scans/min were performed. This delay time enabled the initial peak areas to be determined, which were used to calculate conversion (discussed below).

Figure 3:
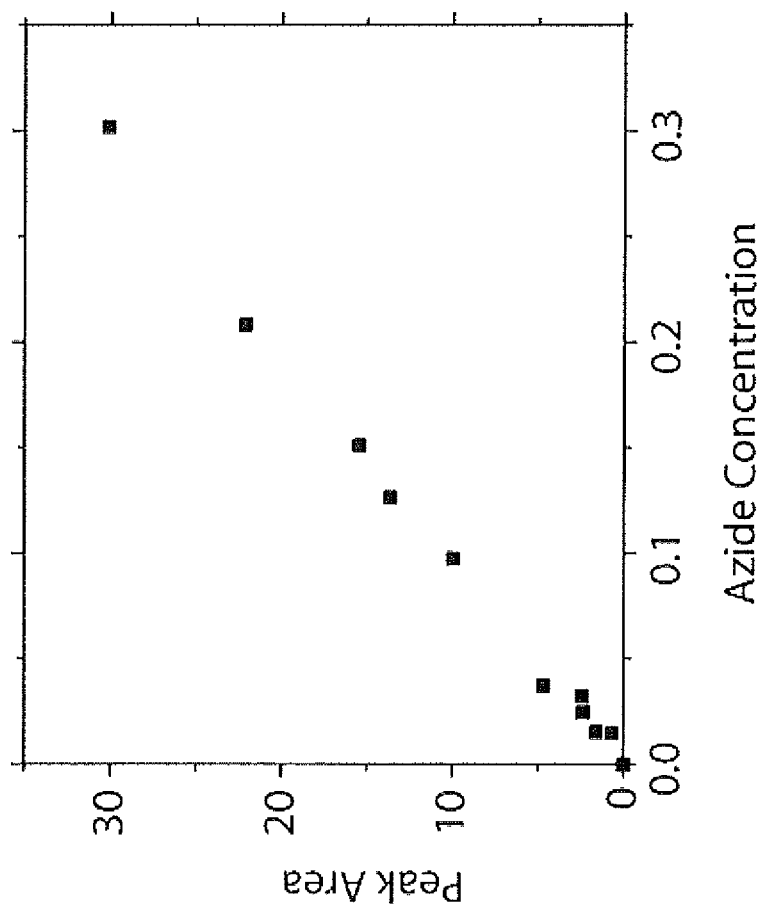
FIG. 3 is a graph illustrating the determination of the extinction coefficient of ethyl azidoacetate in dimethylformamide.

The IR spectrum of ethyl azidoacetate and DMF solutions clearly showed the expected asymmetric azide vibration at 2,109 cm$^{-1}$ that was convoluted with the DMF peaks nearby (Lieber et al., 1957, Infrared Spectra of Organic Azides 29(6): 916). In the region between 2,213 and 1,900 cm$^{-1}$ the contribution of the azide group was calculated by subtracting the DMF spectrum from the solution spectrum. When plotted against concentration (FIG. 3), the peak area shows linear behavior that gives an extinction coefficient ($\epsilon$) of 1.51±0.03 M$^{-1}$μm$^{-1}$. Although an alkyne peak was observed in that range, its extinction coefficient was two orders of magnitude less than the azide.

To analyze the reaction the initial conversion was calculated using the extinction coefficient, pathlength (l), initial concentration ($c_o$), initial peak area ($A(t_o)$), and area ($A(t)$), as shown in the following equation:

$$X=1-\{[A(t)-[A(t_o)-\epsilon \cdot l \cdot c_o]/\epsilon \cdot l \cdot c_o\}$$

Figure 4:
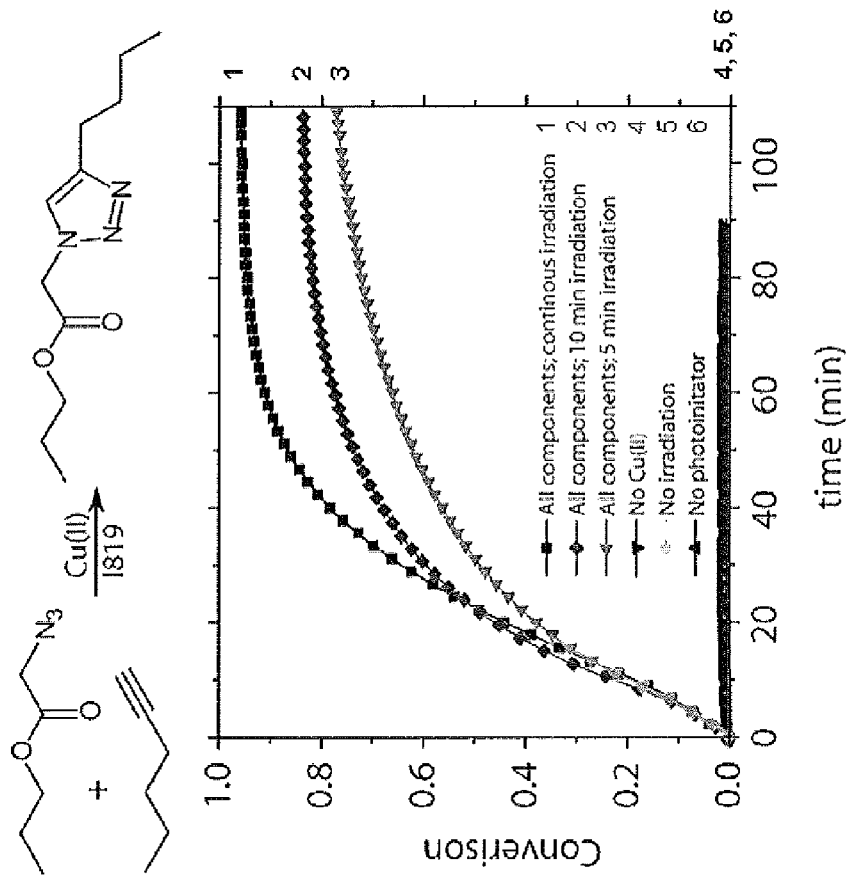
FIG. 4 is a graph illustrating the photo-CuAAC reaction kinetics for continuous irradiation (curve 1), 10 min irradiation (curve 2) and 5 min irradiation (curve 3), in terms of conversion of azide species as a function of time. Also illustrated are the kinetics for azide conversion for mixtures lacking Cu(II) (curve 4), irradiation (curve 5) or photoinitiator (curve 6). No significant reaction was observed for any of these control samples (for which the lines overlay).

These experiments showed a maximum rate 9×10$^{-2}$ mM/s, which is comparable with sodium ascorbate and copper sulfate systems. Control experiments, where the light, initiator, and copper were absent, indicated that each component is necessary and thus support the proposed mechanism (FIG. 4). Off-stoichiometric experiments further verified the absence of side reactions such as Eglintin coupling.

The persistence of catalytic Cu(I) was explored by monitoring the reaction behavior following irradiation cessation (i.e., turning off the light), and prior to complete reactant consumption. This investigation suggested that, once initiated, the reaction persists for extended times in the dark (FIG. 4). In one aspect, this continuing reaction suggested that Cu(I) is not rapidly consumed during the dark reaction (i.e., after the irradiation is ceased), suggesting that the disproportionation of Cu(I) to Cu(II) and Cu(0) occurs over a timescale longer than that of the CuAAC reaction (as radicals are no longer available for reduction). This persistent behavior of Cu(I) enabled complete reaction to be achieved with a minimal amount of required irradiation. For example, a sample irradiated for five minutes, reached 20% conversion during irradiation, but still proceeds to 80% conversion after 160 minutes in the dark. Accordingly, in a continuously irradiated sample each photon absorbed resulted in the reaction of approximately 20 azide and alkynes, while a sample irradiated for 5 minutes produces at least 130 reaction-events per absorbed photon.

Example 3

Photopolymerization of a Hydrogel, as Monitored by Rheometry

Direct monitoring of the extent of reaction in hydrogels is often difficult owing to both the dilute nature of the reactants and the formation of an incipient gel. In such systems, dynamic mechanical analysis (DMA) has emerged as a useful technique for measuring the time evolution of the mechanical properties and as an indirect measure of the extent of reaction. While such measurements do not provide detailed kinetic information, the emergence of a plateau modulus demonstrates the formation of a crosslinked solid and the gelation time enables determination of sufficient exposure times for both polymerizations and in situ patterning.

Temporal control of material forming reactions increases their ease of use. In one aspect, the CuAAC reaction is characterized by its high conversion and functional group tolerance, allowing efficient orthogonal synthesis as well as the facile modification of materials (such as surfaces and polymers). The spatial control enabled by photopolymerization should extend the capability of the CuAAC reaction in creating patterned devices, materials and structures. Hence, the synthesis and in situ modification of hydrogels (an important class of polymers that show promise as tissue mimics), as well as alkyne functionalized silica surfaces, were explored.

In these experiments, a 36 mM solution of Irgacure 2959 and copper sulfate pentahydrate was prepared with deionized water and combined with a stoichiometric mixture of 3K molecular weight PEG dialkyne and 10K molecular weight PEG tetraazide so that the polymers comprised 13.5% of the total mass, and an azide and alkyne concentration of 40 mM.

Figure 5:
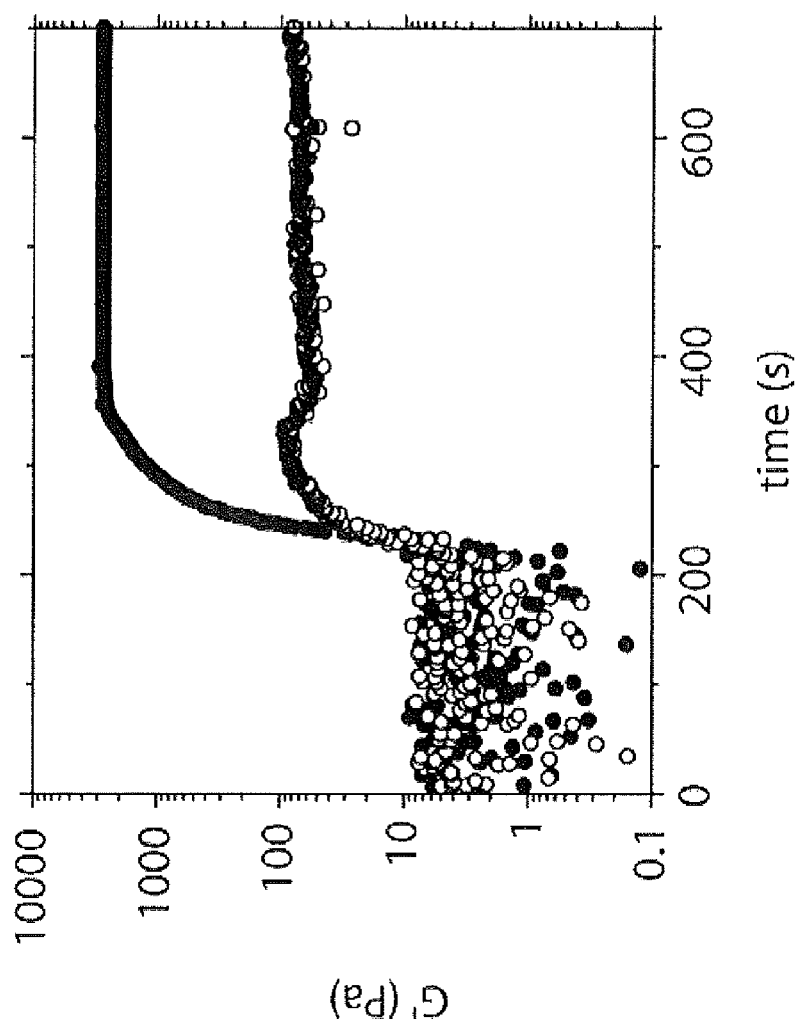
FIG. 5 is a graph illustrating the photopolymerization of a hydrogel, as exemplified in Example 3. The graph illustrates the evolution of the storage (●) and loss moduli (○) during the photocuring of a 10K tetraazide and 3K dialkyne functionalized PEGs at an intensity 100 mW/cm$^2$ (365 nm). The crossover of the moduli occurred near the detection of the instrument at approximately 10-20 Pa.
Figure 6:
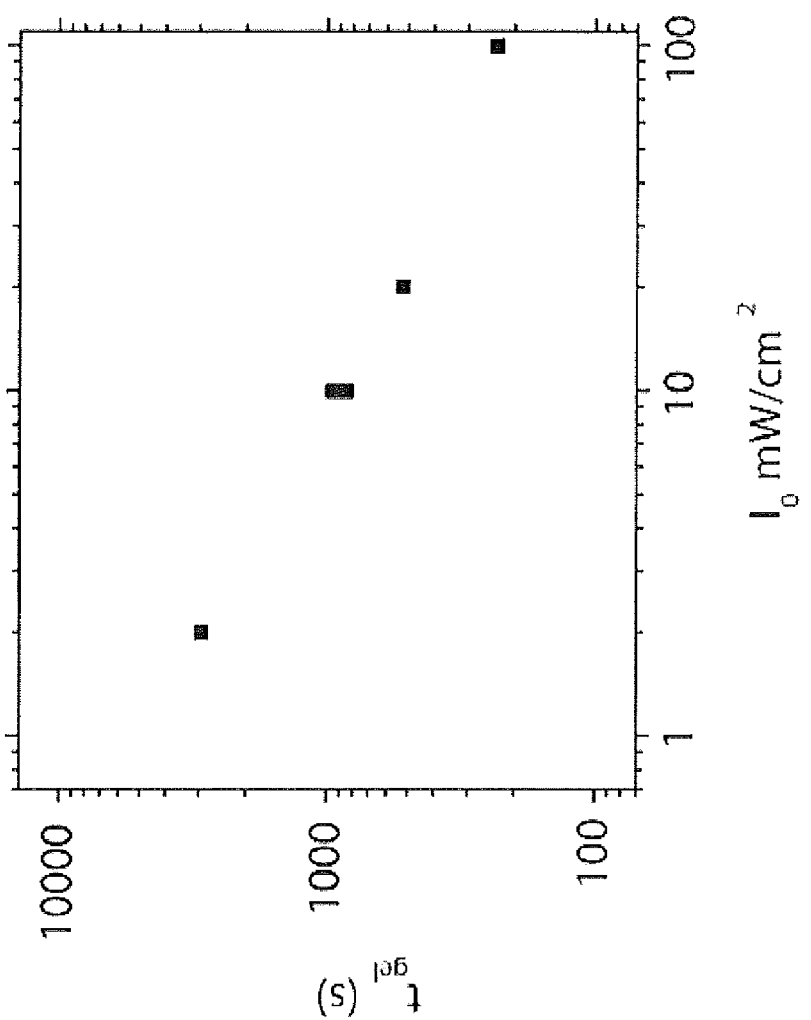
FIG. 6 is a graph illustrating the dependency of time to gel versus light intensity, as exemplified in Example 3. The time for samples to reach a storage modulus of 10 Pa, assigned as the gel-point, is illustrated for several intensities.

A TA Ares rheometer with a parallel plate geometry employing a 20 mm quartz plate was used in all experiments. An EXFO Ultracure high pressure mercury vapor arc lamp with a 365 nm bandpass filter was used for irradiation. A constant strain of 10% and a frequency of 10 rad/s were used. The gap was less than 250 μm for all experiments, allowing for approximately 90% transmission of light. Post-polymerization strain sweeps showed strains of 0.5 to 10% to be in the linear region at the applied frequency. Post-polymerization frequency sweeps showed a constant modulus over time for the entire frequency range considered (1-100 rad/s). The gel point was taken to be the emergence of a storage modulus an order of magnitude above the noise (FIG. 5). All of these values yield identical scaling constants of −0.72±0.3 for a log-log plot of gelation time versus light intensity result (FIG. 6). More rigorous criteria could not be applied due to the rapid time for gelation and non-linear behavior at higher strains. However, such experiments were sufficient to interpolate exposure times for various light intensities.

As illustrated above, multifunctional azide and alkyne functionalized PEG monomers were readily synthesized and irradiated in the presence of copper (II) sulfate and photoinitiator, yielding hydrogels that were formed in less than four minutes (as determined by rheometry). The time to gel was comparable with gels formed by similar concentrations of Cu(II) and sodium ascorbate, and was easily controlled by varying the light intensity. As a consequence of the reduced functional group concentration, the ratio of Cu(II) to functional groups was much higher, and the reaction appears to proceed faster. Uniquely, this photopolymerization appeared to proceed by a step growth mechanism, an attribute of photopolymerizations that is currently shared only with the thiol-ene and thiol-yne photopolymerization reactions. Compared to chain growth polymerizations, this mechanism allows for delayed and readily predicted gel-point conversions. The nearly ideal hydrogels formed by the CuAAC reaction were shown to possess improved mechanical properties compared to networks formed by radical crosslinking of diacrylates. Further, it was shown that the cytotoxic Cu(I) from the CuAAC reaction can be removed by ethylenediamine-tetraacetic acid (EDTA).

Example 4

Gel Patterning

The spatial resolution of a photolithographic process is either limited by the ability of the optics to project the desired image, or the capability of the photoinduced process to reproduce the image. The persistence of Cu(I) in the previous experiments suggested that the diffusivity of Cu(I) may be an important consideration, and taking the diffusivity of Cu(I) to be on the order of $10^{-5}$ cm$^2$/s, a characteristic distance of hundreds of micrometers was calculated for relevant experimental timescales.

Gel patterning experiments were then performed to evaluate effects of translational diffusion of Cu(I). In these experiments, a solution was prepared in identical proportions to those used in the experiments described in Example 3. PEG 100K was added so that the final solution was 10% PEG 100K by mass. The addition of the linear polymer enabled the liquid to be readily spin coated on an alkyne functionalized glass slide. Slides were spin coated using a Speedline Technologies Model P6700 at an initial speed of 750 rpm for 30 seconds and then a final speed of 4,000 rpm for 60 seconds (ramp times were 20, 10, and 5 seconds). The slides were then exposed for 500 seconds in an OAI Hybraalign series 200 Mask Alignment system using a Photronics chrome mask. The light intensity was 35 mW/cm$^2$. After exposure, the slides were immediately immersed in deionized water to remove un-reacted, un-bound material, leaving patterned hydrogel on the glass slide.

Figure 7:
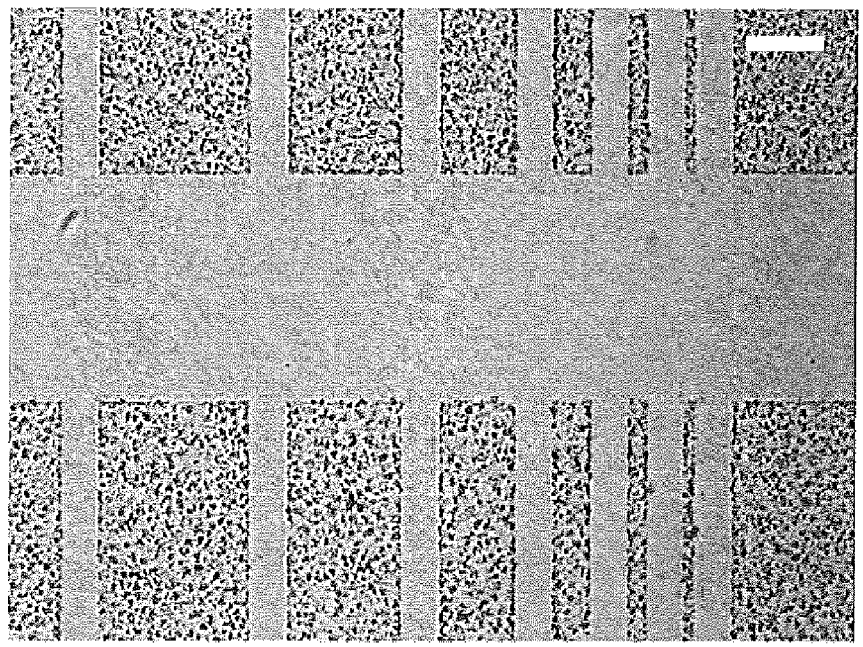
FIG. 7 is an illustration of hydrogel formation as patterned by photo-CuAAC reaction. The inset brightfield image on the right illustrates dehydrated gels formed in the irradiated area on a glass substrate by reacting a 10K molecular weight tetraazide with a 3K molecular weight dialkyne in the presence of a photoinitiator and copper sulfate. The scale bar represents 200 µm, and the gels are 4 µm thick. The photomask comprises 25 µm, 50 µm, 100 µm, 200 µm, 300 µm, and 400 µm bars separated by 100 µm spaces.
Figure 7:
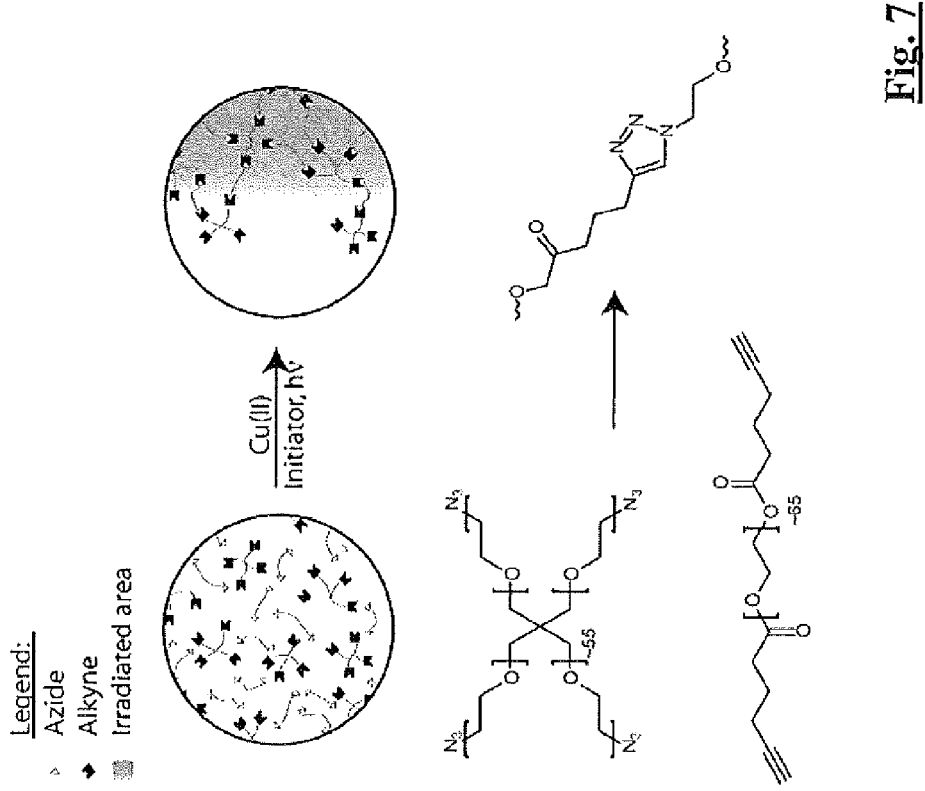

These patterning experiments readily produced 35 micron wide (4.2 micron depth) features that were only 5 µm wider than the mask (FIG. 7). This illustrative result suggested that translational diffusion of Cu(I) was greatly limited by the nature of the reaction. Potential non-limiting explanations for this observation may be: (i) the binding of Cu(I) to the alkyne functionalized monomer during the course of the CuAAC reaction resulted in the diffusion being dictated by the dynamics of the telechelic polymer rather than Cu(I); (ii) the binding of the Cu(I) with the triazole product resulted in a similar decrease in diffusion of Cu(I); (iii) Cu (I) was rapidly consumed once it diffused out of the irradiated area, likely via reactions with oxygen. If oxidation of Cu(I) was at least partially responsible for the resolution of the system, oxygen plays a much different role in these systems than it does in other Click reactions, such as thiol-ene and thiol-yne reactions. In a non-limiting aspect, pattern resolution could be improved by the intentional addition of an oxidizer that would decrease the diffusion of Cu(I) outside of the irradiated area. Regardless, the resolution of this process is suitable for numerous surface and 3D material patterning applications such as the construction of hydrogel based microreactors.

Example 5

In Situ Gel Patterning

Post-synthetic modification of hydrogels was evaluated according to the experiments outlined below. A 13.5 wt % PEG solution of 10K PEG tetrathiol and 3K PEG dialkyne (thiol to alkyne ratio=0.95) was prepared with 0.8% wt. (36 mM) Irgacure 2959, To increase the viscosity of the mixture and enable spin casting of the solution, PEG 100K was added such that the final formulation was 10% PEG 100K by mass. This mixture was then spin-coated on slides functionalized with thiol groups using the same procedure as for the patterned gels (see previous section) and irradiated for 50 s. The slides were subsequently immersed in deionized water for approximately 30 minutes.

Figure 8:
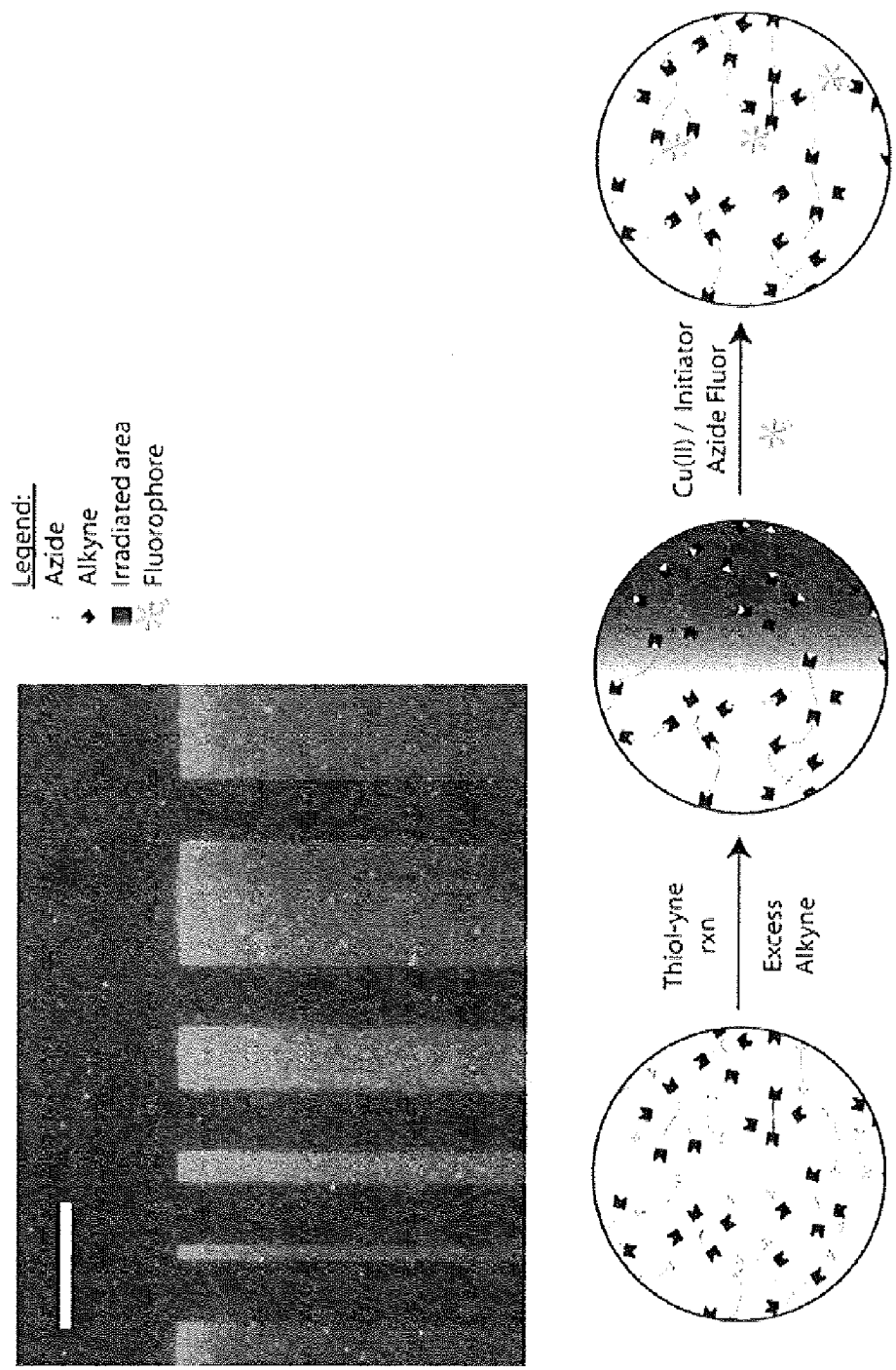
FIG. 8 is an illustration of fluorescent patterning of a hydrogel by the photo-CuAAC reaction. The in situ patterning of a hydrogel (inserted photo) was achieved by first forming an alkyne rich gel via the thiol-yne click reaction of a 10K tetrathiol and 3K dialkyne (scheme at the bottom). A solution of photoinitiator, Cu(II) sulfate, and an azide-labeled fluorophore was then swollen into the gel. Irradiation with a photomask (same mask as FIG. 7) resulted in the generation of Cu(I) in the irradiated areas and the subsequent photo-CuAAC reaction between the pendant alkyne groups and azide functionalized fluorophore. After removal of the unreacted fluorophore, widefield microscopy revealed the pattern of the fluorophore. Scale bar corresponds to 200 µm.
Figure 9A:
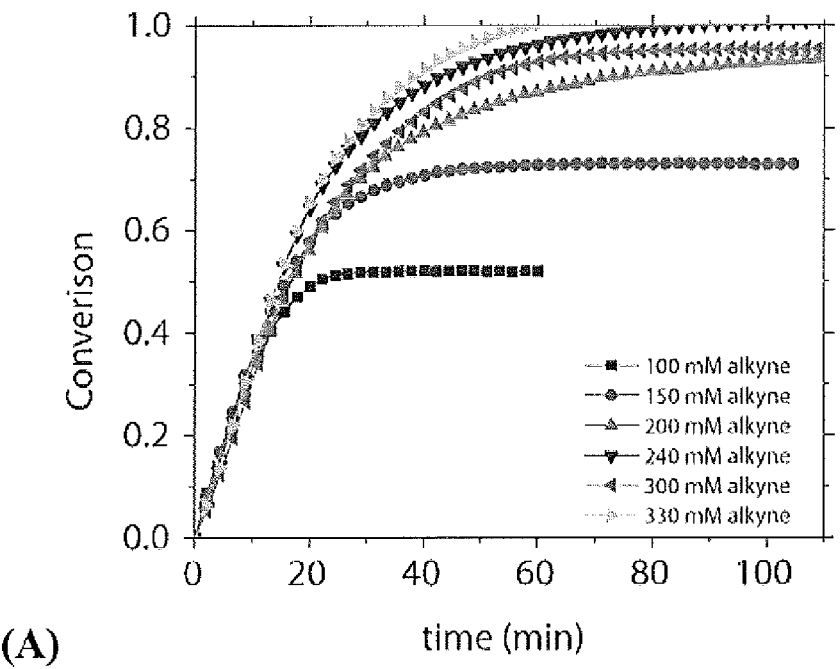
FIGS. 9A-9E, is a set of graphs illustrating the conversion of ethylazidoacetate as a function of time from commencement of irradiation. These experiments were used to calculate the initial rates for FIGS. 10, 11, and 13.
Figure 9B:
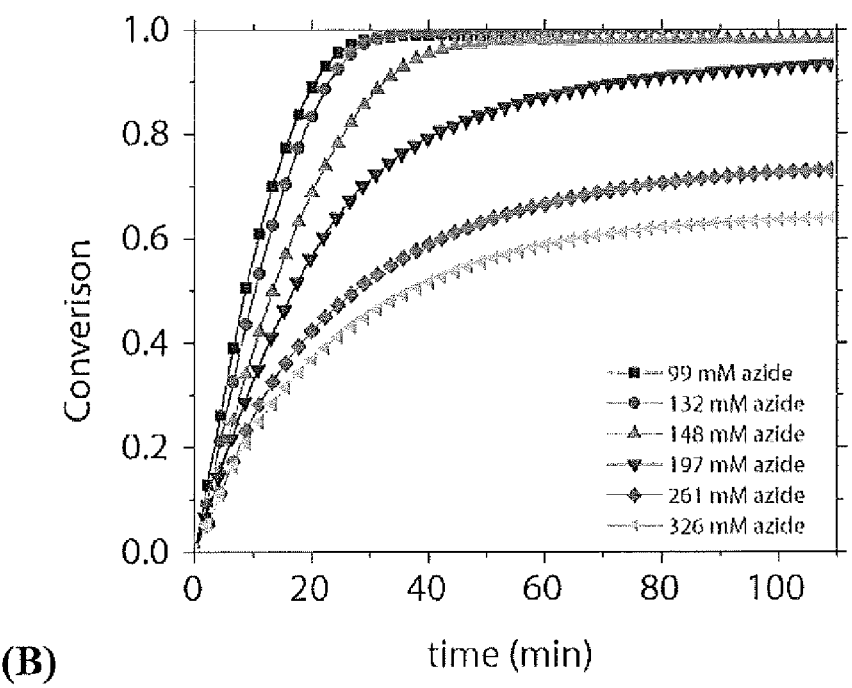
Figure 9C:
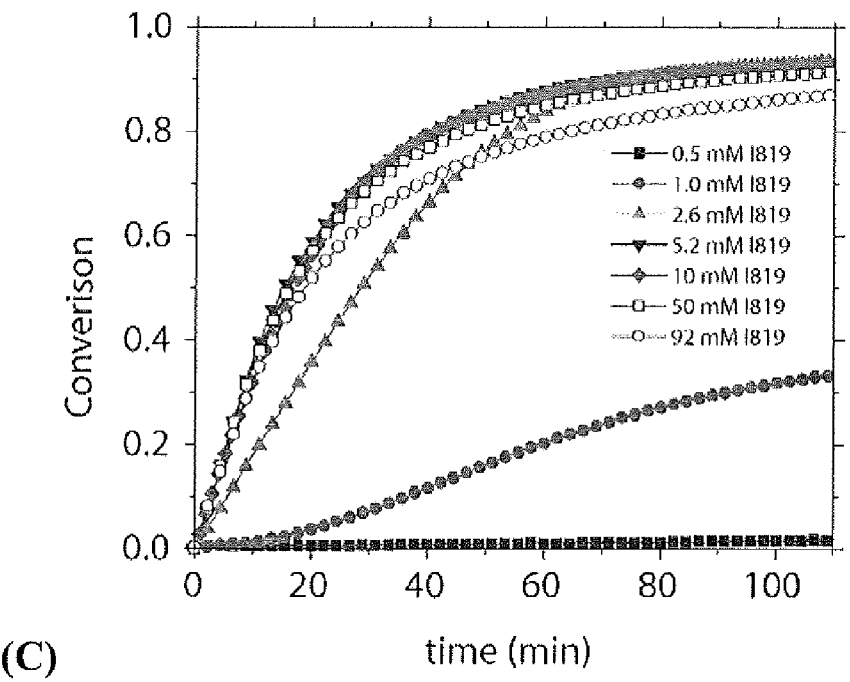
Figure 9D:
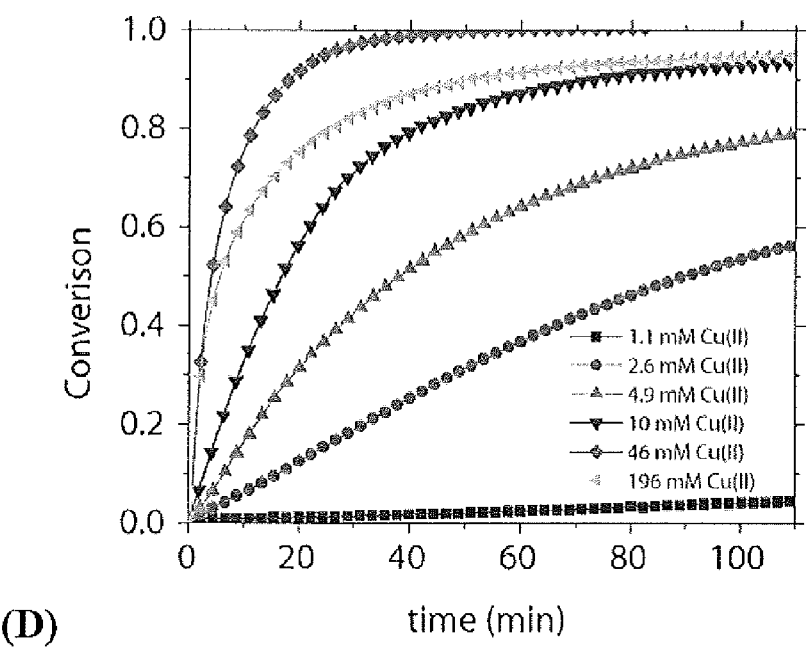
Figure 9E:
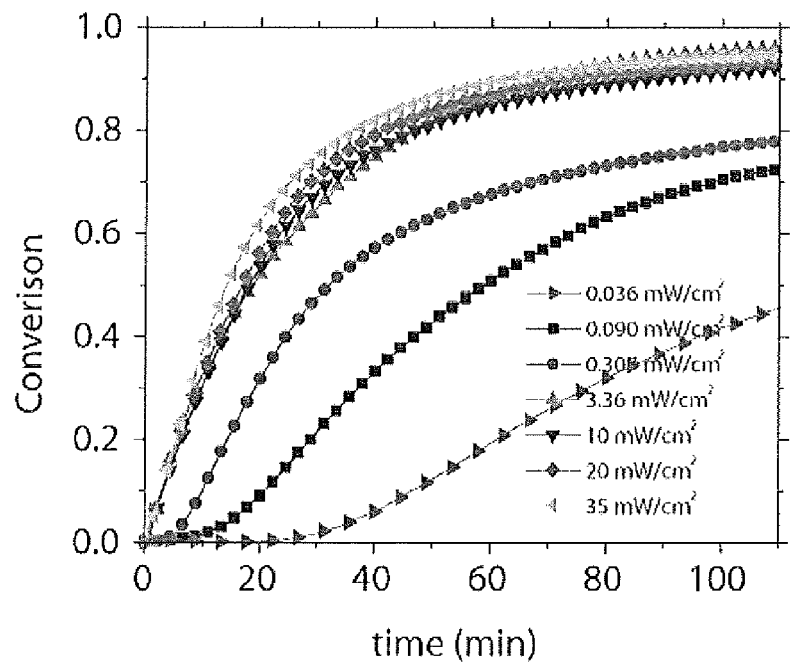

A solution of 36 mM Irgacure 2959, 36 mM copper (II) sulfate pentahydrate, and 0.4 mM Alexa Fluor 488 5-carboxamide-(6-azidohexanyl), bis(triethylamine salt) was then swollen into the gel for 30 minutes before the samples were irradiated for 50 seconds. Afterwards the gels were soaked in deionized water for several minutes to remove residual fluorophore. The results are illustrated in FIG. 8.

As described above, gels were synthesized by the thiol-yne reaction with a stoichiometric excess of alkynes. A solution of photoinitiator, copper (II) sulfate, and a functionalized fluorophore was then swollen into the gel. Upon irradiation, the CuAAC reaction between the functionalized fluorophore and the pendant alkynes in the polymer network produced a fluorescent pattern within spatially defined regions of the gel. As illustrated in FIG. 8, 25 µm features could readily be formed and discerned with only 50 seconds of irradiation.

As illustrated by the experiments described above, the photochemical generation of chemical species that locally reduce Cu(II) to Cu(I) for catalysis of the CuAAC reaction was studied by a combination of $^1$H-NMR spectroscopy, FTIR spectroscopy, and dynamic mechanical analysis, while confocal and optical microscopies confirmed the fidelity of the patterned features produced using this technique. This approach may be readily adaptable to both aqueous and non-aqueous systems, with the likely limitation being the copper salt solubility. Moreover, a variety of radical generators may be employed. TiO$_2$ and cleavage type photoinitiators were demonstrated herein, and the abstraction type photoinitiators frequently used in copper nanoparticle synthesis and should work equally well. Additionally, the uncanny resemblance of this system to reverse atom transfer radical polymerizations (Wang et al., 1995, Macromol. 28(22):7572) suggests that systems could be designed to form persistent radicals. Not only would this allow for simultaneous Click reactions and living polymerization, but some atom transfer radical polymerizations are capable of utilizing mere ppm levels of copper, suggesting perhaps that this approach could enable a dramatic reduction in the copper concentration. In one aspect, this reduction could permit the CuAAC reaction to be utilized in biological systems as the irradiation conditions and initiators used are cytocompatible. In conclusion, this approach to catalysis of the CuAAC reaction is broadly applicable, improving the implementation, robustness and control of the CuAAC reaction.

Example 6

As described herein, a more thorough understanding of the kinetics and mechanisms involved in the photo-mediated catalysis of the CuAAC reaction was developed through a series of initial rate experiments. In a typical experiment, a solution of dimethylformamide (DMF) with 200 mM ethyl azidoacetate, 200 mM 1-hexyne, 10 mM copper sulfate pentahydrate, and 10 mM I819 was injected into the liquid cell. Samples that were noted as being sparged had either ultra high purity argon or oxygen bubbled through them for 15 minutes.

Figure 10:
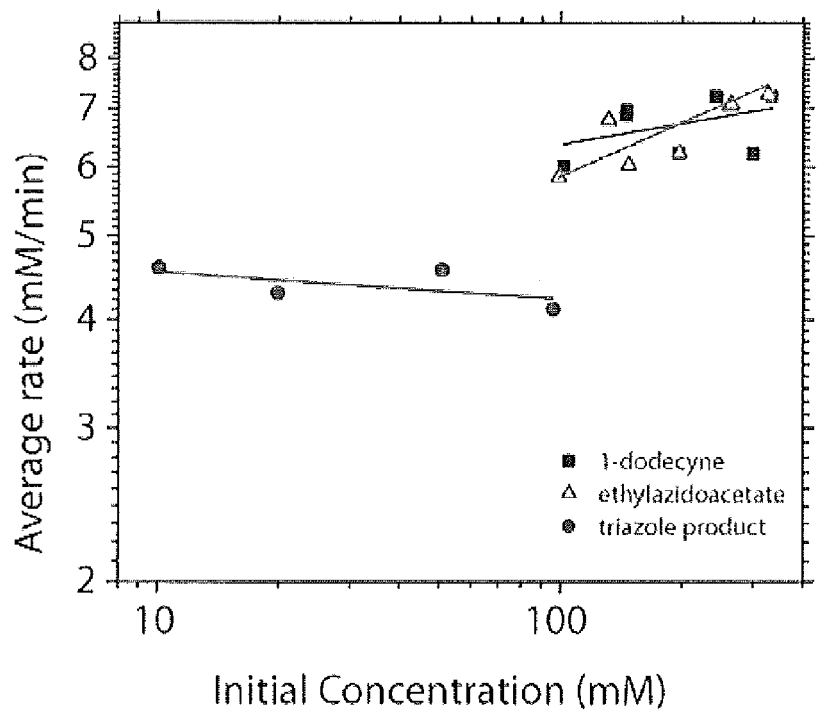
FIG. 10 is a graph illustrating the dependence of the reaction rate on the initial concentrations of 1-dodecyne, ethylazidoacetate, and triazole product. The data revealed that the rate was approximately independent of all three (the slopes are 0.08±0.07, 0.16±0.07, and −0.03±0.03, respectively) The concentration of the non-varying component was 200 mM for all experiments. The photoinitiator and copper sulphate concentrations were both 10 mM, and the irradiation intensity was 20 mW/cm$^2$ for all experiments.

The CuAAC reaction was monitored using Fourier transform infrared (FTIR) spectroscopy, which allows for in situ measurement of azide and alkyne concentrations. Throughout these experiments model compounds were used in solution to simplify the analysis and avoid problems such as the onset of vitrification, which regularly occurs during the polymerization of materials with sub-ambient glass transition temperatures. The click nature of the CuAAC reaction suggests that the behaviour observed from this model pair of reactants may be extrapolated to a wide range of azides and terminal alkynes. However, it should be noted that the specific substitution of the triazole may play some role (Rodionov et al., 2007, J. Am. Chem. Soc. 129:12705-12712). Initial rate experiments performed with ethylazidoacetate and 1-dodecyne at catalytic concentrations of copper(II) and photoinitiator (ca. 20 to 1 molar ratios) verified the overall reaction rate to be nearly independent of both azide and alkyne concentrations (FIG. 10). Consequently, zero order kinetics were observed until approximately 40% to 60% of the limiting reagent was consumed. Beyond this regime, non-linear behaviour was observed, consistent with the mechanism of the reaction shifting to a different rate law as the concentrations of the reactants and copper catalyst became similar. The zero order kinetics and the shift in the reaction mechanism was consistent with previous measurements of benzylazide and phenylacetylene (Rodionov et al., 2005, Angew. Chem.-Int. Edit. 44:2210-2215). Such behaviour is believed to be the general case for the CuAAC reaction in the absence of added accelerating ligands (Rodionov et al., 2007, JACS 129: 12705-12712). The independence of the reaction rate on alkyne and azide concentrations would tentatively imply that the regeneration of the Cu(I) is typically the rate-limiting step (reaction III in FIG. 1A). This behavior then suggests that if the generation of Cu(I) is rapid, as in the case of reduction by sodium ascorbate, that the CuAAC reaction mechanism is not influenced by the method used to reduce Cu(II).

Figure 11:
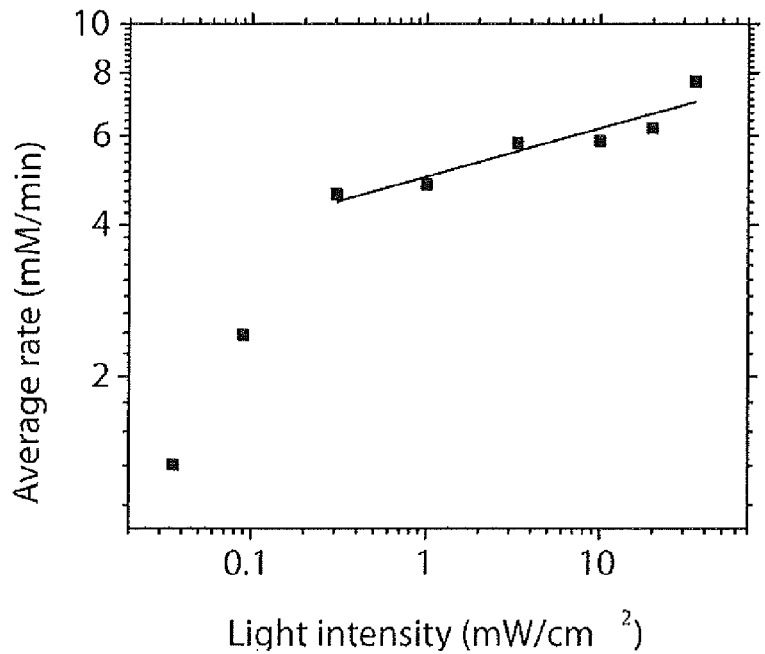
FIG. 11 is a graph illustrating the effect of irradiation on the CuAAC reaction rate. For irradiation intensities greater than 0.3 mW/cm$^2$ the effect of light intensity on the reaction rate was negligible with a scaling constant equal to 0.097±0.02 while for lower light intensities, the scaling exponent was found to be approximately 1.5. The azide and alkyne concentrations were 200 mM each, and the photoinitiator and copper sulphate concentrations were both 10 mM for all experiments.

The reaction rate dependence on irradiation intensity is nearly zero-order (0.097±0.02) at irradiation intensities greater than approximately 0.3 mW/cm$^2$ (FIG. 11). The irradiation intensity was proportional to the photolysis rate, and therefore the rate at which radicals were generated. Consequently, the independence of the reaction rate on the light intensity implied that the generation of radicals is fast relative to the rate limiting step. As in the case of reduction by sodium ascorbate, the cycloaddition appears to be the rate-limiting step. This outcome is not surprising as the half-life of I819 at 20 mW/cm$^2$ is approximately 36 seconds. Comparatively, over the first 36 seconds less than two percent of the azide was consumed by the CuAAC reaction. When the timescales of photolysis and the CuAAC reaction became comparable, i.e., here at much lower light intensities, it was expected that the reaction rate would no longer be independent of the light intensity. In FIG. 11 it was observed that the scaling value of the light intensity did indeed increase at irradiation intensities less that 0.3 mW/cm$^2$, which corresponds to when the half-life of the photoinitiator is calculated to be of the same order as that of the CuAAC reaction itself.

Figure 12:
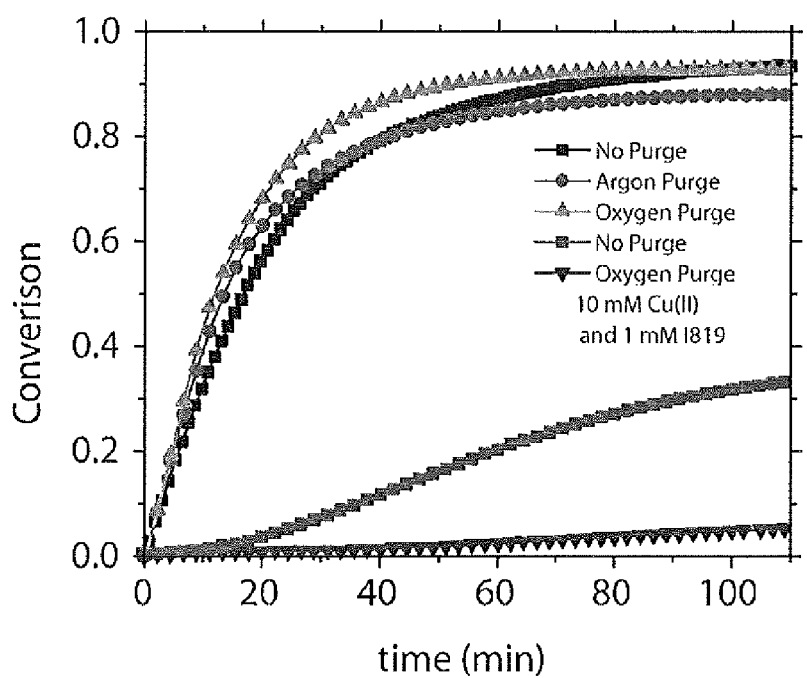
FIG. 12 is a graph illustrating results of kinetic experiments. When the concentration of photoinitiator and Cu(II) were both 10 mM, sparging with oxygen had no effect on the reaction kinetics. When the concentration of photoinitiator was reduced to 1 mM, radical scavenging by oxygen significantly retarded the CuAAC reaction. The azide and alkyne concentration were each 200 mM, and the irradiation intensity was 20 mW/cm$^2$ for all experiments.

FIG. 12 shows that the reaction kinetics for samples containing equimolar concentrations of photoinitiator and Cu(II) prepared under ambient conditions possessed a similar reaction rate to those sparged with argon or oxygen. When the ratio of photoinitiator to Cu(II) was reduced, oxygen significantly retarded the CuAAC reaction. Oxygen is highly reactive towards phosphinoyl and benzoyl radicals, and the resulting peroxy radicals are incapable of reducing Cu(II). (Buettner & Jurkiewicz, 1996, Radiat. Res. 145:532-541). In contrast, equimolar mixtures of Cu(II) and photoinitiator did not exhibit an induction period. The lack of inhibition is explained by the excess of radicals from the photoinitiator, which ensured complete consumption of Cu(II), even though a fraction of the radicals was scavenged by oxygen. Unlike some systems utilizing Noorish type II photoinitiators, the excess radicals eliminated the need for rigorous purging of oxygen (Ritter & Konig, 2006, Chem. Commun. 4694-4696). Importantly, the data also indicated that oxygen does not irreversibly consume Cu(I). If oxygen did irreversibly consume Cu(I) then the reaction rates of all the equimolar cases would not be similar. Cu(I) reactions with oxygen may be prevented by ligand coordination or effectively reversed by the excess of radicals.

Figure 13:
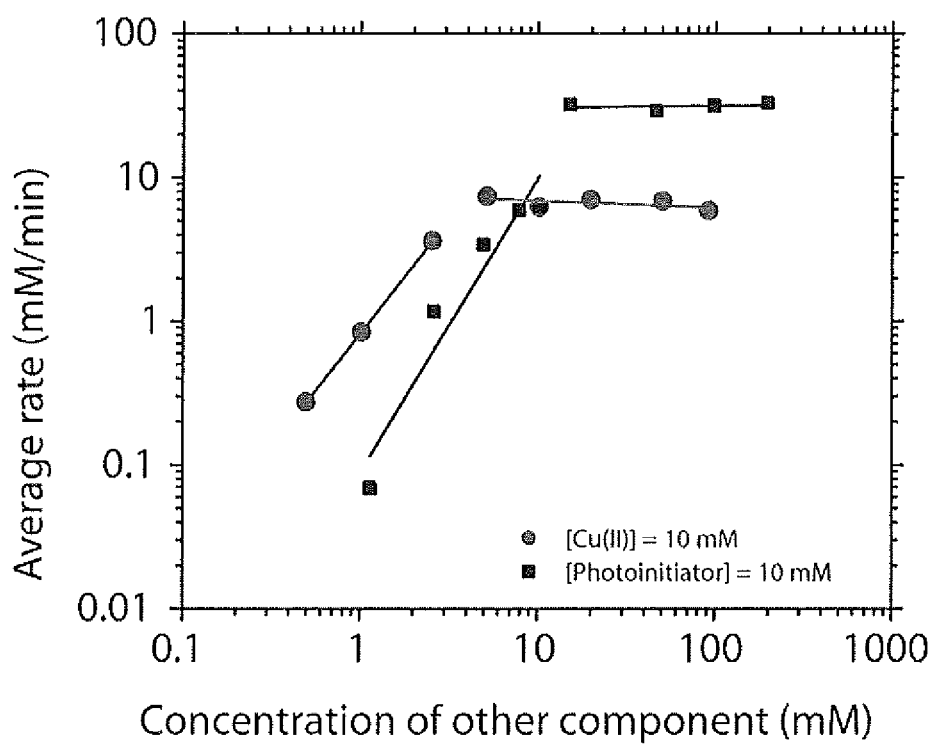
FIG. 13 is a graph illustrating the average reaction rate versus the initial concentrations of Cu(II) and photoinitiator (red circles and black squares, respectively). This experiment revealed two distinct regimes. When Cu(II) was in excess, Cu(II) showed a scaling constant of 0.01±0.03 and the photoinitiator scaled with an exponent of 1.58±0.004. When the photoinitiator was in excess, the Cu(II) showed a scaling constant of 2.0±0.3, and the photoinitiator scaled with an exponent of −0.05±0.04

The dependence of the reaction rate on copper and photoinitiator was significantly more complicated. When the photoinitiator concentration was held constant at 10 mM the reaction rate showed an abrupt change in scaling at an initial Cu(II) concentration of approximately 15 mM (FIG. 13). Above the threshold value of 15 mM of Cu(II), the reaction rate became largely independent of the initial Cu(II) concentration. The concentration of Cu(I) resulting from the reduction of Cu(II) could either be limited by the amount of photoinitiator available to reduce Cu(II), or from the resulting disproportionation/comproportionation equilibrium. The independence of the reaction rate from the initial Cu(II) concentration implies that while disproportionation of Cu(I) is highly thermodynamically favorable and typically rapid, it did not occur in this system. If disproportionation were occurring, the initial addition of excess Cu(II) would shift the equilibrium to produce more Cu(I) and the reaction rate would increase. Ligands that bind Cu(I) can protect it from disproportionation by shifting the equilibrium from favoring disproportionation (log $K_{Disp}$=4.26; Tsarevsky et al., 2007, J. Organomet. Chem. 692:3212-3222.) to comproportionation (log $K_{Disp}$=−2.20; Matyjaszewski et al., 2007, Macromolecules 40:7795-7806). In this system the ligands responsible for this behaviour may be the triazole products, which are known to protect Cu(I), or the reactants themselves. The lack of an inhibition time and the absence of autocatalysis suggested that the protecting ligand is present at the beginning of the reaction, implying the alkyne reactant is the protecting agent. However, as the triazole concentration was greater than that of Cu(I) after 5% conversion, the resolution of these experiments may not be sufficient to detect a slight inhibition during the timeframe that the protecting ligand is formed.

Likewise, when the initial Cu(II) concentration was held constant at 10 mM, the reaction rate showed an abrupt change in scaling at a photoinitiator concentration of 5 mM. Above this threshold concentration of photoinitiator, the reaction rate was independent of photoinitiator concentration. If the reduction of Cu(I) to copper metal were occurring, it would be expected that adding more photoinitiator would result in more radicals and less Cu(I). As the CuAAC reaction rate typically shows a second order dependence on Cu(I) concentration (Rodionov et al., 2005, Angew. Chem.-Int. Edit. 44:2210-2215; Rodionov et al., 2007, JACS 129:12705-12712) it would be expected that increasing the initial photoinitiator concentration would reduce the CuAAC reaction rate. The independence of the CuAAC reaction rate at higher photoinitiator concentrations implied that the reduction of Cu(I) to copper metal is not occurring to a significant extent under these conditions in this system. Radical reduction has previously been used to synthesize copper nanoparticles (Sakamoto et al., 2009, J. Photochem. Photobiol. C-Photochem. Rev. 10:33-56). However, the alkyne or triazole ligands appear to protect Cu(I) from each of these three side reactions: oxidation by dissolved oxygen, disproportionation, and further reduction by radicals. Indeed formation of copper metal was noted only when working with very dilute hydrogels where the concentration of Cu(II) was nearly equimolar with the reactants.

In both the case of Cu(II) and the photoinitiator the threshold behavior appeared to result solely from a change in the limiting reagent. The threshold values suggested that each molecule of I819 results in the reduction of 1.5 to 2 molecules of Cu(I). As I819 can produce two benzoyl and two phosphinoyl radicals, this would suggest that either one of the radicals was ineffective in reducing Cu(II), or that the initiator fragments were no longer photoactive to visible light and could not generate a second pair of radicals.

Below the threshold initial Cu(II) concentration of 15 mM, the reaction rate displayed a second order dependence on the initial concentration of Cu(II). In the absence of disproportionation and reduction of Cu(I) to copper metal, it would be expected that all of the Cu(II) would be reduced to Cu(I) by the excess radicals that are generated. Indeed, the scaling constant is measured to be 2.0±0.3, consistent with previous measurements (Rodionov et al., 2005, Angew. Chem.-Int. Edit. 44:2210-2215; Rodionov et al., 2007, JACS 129:12705-12712). Below the threshold photoinitiator concentration of 5 mM, the reaction rate showed a reaction order of 1.58±0.01. When Cu(II) was in excess, it would be expected that the amount of Cu(II) reduced to Cu(I) would be proportional to the initial photoinitiator concentration, which would result in a second order dependence of the CuAAC reaction rate on the photoinitiator concentration. The scaling exponent of 1.58 instead of 2.0 implies that as the photoinitiator concentration was increased, unproductive radical reactions such as primary radical recombination, i.e., radical-radical termination, became more prevalent. This value was similar to the scaling exponent of 1.5 that the light intensity appeared to approach at its lower extreme (FIG. 11). It was expected that both the light intensity and initial radical concentration should have similar scaling constants under these conditions.

These results suggest that the photo-catalyzed CuAAC reaction is controlled not by the rate of generation of Cu(I), but rather the amount of Cu(I) generated. Like sodium ascorbate, conventional photoinitiators rapidly reduce Cu(II) under typical conditions. When used in a polymerization reaction, these attributes would make the photo-mediated CuAAC reaction quite different from the typical radical photopolymerization where the rate of polymerization depends on the rate of active species generation. Further, the results suggest oxidation by dissolved oxygen, disproportionation, and further reduction of Cu(I) by radicals are all suppressed in these systems. This likely occurs because of Cu(I) coordination with either the alkyne or triazole ligands that are present. This behaviour explains both the dark cure reaction previously noted, and the high fidelity of the patterning previously observed, as Cu(I) spends much time bound to less diffusive species. As these side reactions are suppressed, this demonstrates that large excesses of conventional photoinitiators are not required to continually regenerate Cu(I), as is the case when sodium ascorbate is used as the reductant. Thus, when designing a reaction, workers need only to consider the tendency of the azides to decompose when exposed to short wavelength UV radiation and choose a photoinitiator appropriately. Finally, these experiments indicate that understanding catalyst turnover could be key to reducing catalyst concentration in real systems such as bulk polymerizations, surface modifications, and particle functionalizations.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising an alkyne-based substrate, an azide-based substrate, at least one Cu(II) salt and at least one photoinducible reducing agent,
    wherein said alkyne-based substrate comprises at least one reactive alkynyl group,
    wherein said azide-based substrate comprises at least one reactive azide group, and
    wherein exposure of at least a portion of said composition to electromagnetic radiation promotes formation of Cu(I), which catalyzes cycloaddition of said at least one reactive alkynyl group and said at least one reactive azide group.

2. The composition of claim 1, wherein said alkyne-based substrate or said azide-based substrate is attached to a hydrogel.

3. The composition of claim 1, wherein said at least one reactive alkynyl group is a terminal alkynyl group.

4. The composition of claim 1, wherein the molar ratio of said at least one reactive alkyne group and said at least reactive azide group in said composition ranges from about $10^{-2}$ to about $10^{+2}$.

5. The composition of claim 1, wherein said at least one photoinducible reducing agent is a Type (I) photoinitiator.

6. The composition of claim 1, wherein said at least one reducing agent is selected from the group consisting of: 1-hydroxy-cyclohexyl-phenyl-ketone; benzophenone; 2-hydroxy-2-methyl-1-phenyl-1-propanone; 2-hydroxy-1-[4-(2-hydroxyethoxy)phenyl]-2-methyl-1-propanone; methyl benzoylformate; oxy-phenyl-acetic acid 2-[2-oxo-2-phenyl-acetoxy-ethoxy]-ethyl ester; oxy-phenyl-acetic 2-[2-hydroxy-ethoxy]-ethyl ester; oxy-phenyl-acetic acid 2-[2-oxo-2-phenyl-acetoxy-ethoxy]-ethyl ester; alpha,alpha-dimethoxy-alpha-phenyl acetophenone; 2-benzyl-2-(dimethylamino)-1-[4-(4-morpholinyl) phenyl]-1-butanone; 2-methyl-1-[4-(methylthio)phenyl]-2-(4-morpholinyl)-1-propanone; diphenyl (2,4,6-trimethylbenzoyl) -phosphine oxide; bis-(eta 5-2,4-cyclopentadien-1-yl)-bis-[2,6-difluoro-3-(1H-pyrrol-1-yl) -phenyl]-titanium; (4-methylphenyl) [4-(2-methylpropyl) phenyl]-iodonium hexafluorophosphate; 2-(4-methylbenzyl)-2-(dimethylamino)-1-(4-morpholinophenyl)-butan-1-one; 4-(2-hydroxyethoxy)phenyl-(2-hydroxy-2-propyl)-ketone; bis-(2,6-dimethoxybenzoyl)-2,4,4-trimethylpentyl phosphine oxide; titanium dioxide; and mixtures thereof.

7. A method of preparing a compound of formula (I):

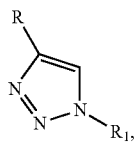  (I)

said method comprising the steps of:
(i) mixing a compound of formula (II):

 (II), a compound of formula (III):

 (III), at least one Cu(II) salt and at least one photoinducible reducing agent, to generate a first composition,
wherein R and $R_1$ are independently alkyl, substituted alkyl, cycloalkyl, substituted cycloalkyl, alkenyl, substituted alkenyl, alkynyl, substituted alkynyl, heteroalkyl, substituted heteroalkyl, heteroalkenyl, substituted heteroalkenyl, aryl, substituted aryl, aryl-($C_1$-$C_3$)alkyl, heterocyclyl, substituted heterocyclyl, heteroaryl, or substituted heteroaryl; and
(ii) exposing at least a portion of said first composition to electromagnetic radiation, whereby said at least one Cu(II) salt is at least partiallty reduced to a Cu(I) species, which catalyzes cycloaddition of said compound of formula (II) with said compound of formula (III) to form said compound of formula (I).

8. The method of claim 7, wherein the molar ratio of said compound of formula (II) and said compound of formula (III) in said first composition ranges from about 0.5 to about 2.

9. The method of claim 7, wherein said at least one reducing agent is a Type (I) photoinitiator.

10. The method of claim 7, wherein said at least one reducing agent is selected from the group consisting of: 1-hydroxy-cyclohexyl-phenyl-ketone; benzophenone; 2-hydroxy-2-methyl-1-phenyl-1-propanone; 2-hydroxy-1[4-(2-hydroxyethoxy)phenyl]-2-methyl-1-propanone; methyl benzoylformate; oxy-phenyl-acetic acid 2-[2-oxo-2-phenyl-acetoxy -ethoxy]-ethyl ester; oxy-phenyl-acetic 2[2-hydroxy-ethoxy]-ethyl ester; oxy-phenyl-acetic acid 2-[2-oxo-2-phenyl-acetoxy-ethoxy]-ethyl ester; alpha,alpha-dimethoxy-alpha-phenyl acetophenone; 2-benzyl-2-(dimethylamino)-1-[4-(4-morpholinyl) phenyl]-1-butanone; 2-methyl-1[4-(methylthio)phenyl]-2-(4-morpholinyl)-1-propanone; diphenyl (2,4,6-trimethylbenzoyl) -phosphine oxide; bis-(eta 5-2,4-cyclopentadien-1-yl)-bis-[2,6-difluoro-3-(1H-pyrrol-1-yl) -phenyl]-titanium; (4-methylphenyl) [4-(2-methylpropyl) phenyl]-iodonium hexafluorophosphate; 2-(4-methylbenzyl)-2-(dimethylamino)-1-(4-morpholinophenyl)-butan-1-one; 4-(2-hydroxyethoxy)phenyl-(2-hydroxy-2-propyl)-ketone; bis-(2,6-dimethoxybenzoyl) -2,4,4-trimethylpentyl phosphine oxide; titanium dioxide; and mixtures thereof.

11. The method of claim 7, wherein said electromagnetic radiation comprises ultraviolet or visible electromagnetic radiation.

* * * * *